United States Patent
Zhang et al.

(10) Patent No.: US 9,920,023 B2
(45) Date of Patent: *Mar. 20, 2018

(54) LEVELING COMPOSITION AND METHOD FOR ELECTRODEPOSITION OF METALS IN MICROELECTRONICS

(71) Applicant: Suzhou Shinhao Materials LLC, Wujiang (CN)

(72) Inventors: Yun Zhang, Warren, NJ (US); Tao Ma, Wujiang (CN); Peipei Dong, Wujiang (CN)

(73) Assignee: Suzhou Shinhao Materials LLC, Wujiang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/388,927

(22) Filed: Dec. 22, 2016

(65) Prior Publication Data

US 2017/0101389 A1 Apr. 13, 2017

Related U.S. Application Data

(63) Continuation of application No. 13/261,924, filed as application No. PCT/CN2014/076807 on May 5, 2014, now Pat. No. 9,551,081.

(30) Foreign Application Priority Data

Dec. 26, 2013 (CN) .......................... 2013 1 0731443
Dec. 26, 2013 (CN) .......................... 2013 1 0731859

(51) Int. Cl.
*C25D 3/00* (2006.01)
*C25D 5/02* (2006.01)
(Continued)

(52) U.S. Cl.
CPC .............. *C07D 311/84* (2013.01); *C25D 3/38* (2013.01); *C25D 3/58* (2013.01); *C25D 7/123* (2013.01); *H01L 21/76873* (2013.01)

(58) Field of Classification Search
CPC ... C25D 3/02; C25D 5/02; C25D 7/12; C25D 7/123
(Continued)

(56) References Cited

U.S. PATENT DOCUMENTS 2,738,318 A * 3/1956 Fellows .................... C25D 3/38
205/297
9,551,081 B2 * 1/2017 Zhang ...................... C25D 3/56

OTHER PUBLICATIONS

Castoldi et al., "The Role of the Organic Additives in the Localized Copper Plating: Flat, Dish and Domed Shape Copper Bumps," ECS Transactions (no month, 2008), vol. 16, No. 14, pp. 23-28. (Year: 2008).*

(Continued)

*Primary Examiner* — Edna Wong
(74) *Attorney, Agent, or Firm* — SZDC Law P.C.

(57) ABSTRACT

The present disclosure relates to a leveling composition for electrodepositing metals. The composition comprises a compound of formula (I):

(Continued)

Profile 3D vision

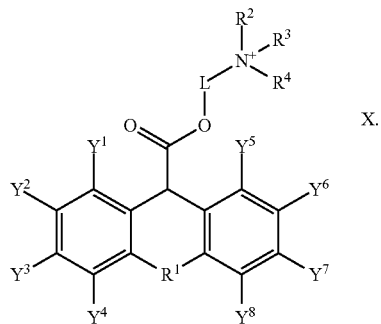

(I)

16 Claims, 27 Drawing Sheets

(51) Int. Cl.
*H05K 3/00* (2006.01)
*C07D 311/84* (2006.01)
*C25D 3/38* (2006.01)
*C25D 3/58* (2006.01)
*C25D 7/12* (2006.01)
*H01L 21/768* (2006.01)

(58) Field of Classification Search
USPC ................................ 205/118, 123, 125, 261
See application file for complete search history.

(56) References Cited

OTHER PUBLICATIONS

Hanaoka et al., "Increase in Electrical Resistivity of Copper and Aluminum Fine Lines," Materials Transactions (no month, 2002), vol. 43, No. 7, pp. 1621-1623. (Year: 2002).*

Meindl et al., "Interconnect Opportunities for Gigascale Integration," IBM J. Res. & Dev. (Mar./May 2002), vol. 46, No. 2/3, pp. 245-263. (Year: 2002).*

* cited by examiner

L113 3A, 2min

L113+S 3A, 2min

L113+S+A  3A, 2min

L26 +S+A 3A, 2min

L113 20um

Profile                    3D vision

LEVELING COMPOSITION AND METHOD FOR ELECTRODEPOSITION OF METALS IN MICROELECTRONICS

The present application is a Continuation of U.S. patent application Ser. No. 13/261,924, filed on Jun. 24, 2014, now U.S. Pat. No. 9,551,081, issued on Jan. 24, 2017, which is a National Phase Application of PCT/CN2014/076807, filed on May 5, 2014, which claims priority to Chinese Patent Application Nos. 201310731443.3 and 201310731859.5, both filed on Dec. 26, 2013, all of which are hereby incorporated by reference in their entirety as set forth herein.

TECHNICAL FIELD

The present invention generally relates to electroplating, electroplating additives, method of electroplating, metal plating; and the use of additives in an electrolytic deposition chemistry, and a method for depositing metal or metal alloys; and more specifically to leveler additives for use in an electrolytic deposition chemistry, and a method for copper metallization in printed wiring board (PWB), semiconductor integrated circuits, microelectromechanic systems (MEMS), surface mount technology (SMD), connectors, base station, light emitting diode (LED), and molded interconnection devices (MID); and even more specifically to leveler additives for use in an copper electrolytic deposition chemistry for semiconductor chip interconnection.

BACKGROUND

Metallic copper is an excellent material for chip interconnection due to its advantages such as good electrical conductivity, high thermal conductivity, low melting point and extensibility. Copper plating is the method of choice for copper interconnection. However, with continued minimization of the chip line width, it becomes harder and harder to deposit copper metal lines without defects. A defect-free copper plating is achieved by integrating seamlessly the plating chemistry, plating tool, and semiconductor chips.

The challenges in acid copper plating have always been 1) leveling effect, 2) said leveling effect over a wide range of aspect ratio (depth:width) preferably found on the same die, 3) achieving the desirable leveling effect at high current densities therefore increasing the manufacturing throughput, 4) levelers that are non-toxic, environmental friendly, 5) levelers that are easily analyzable by conventional means so their concentrations can be monitored and controlled in a plating bath, 6) minimizing by-products which often have detrimental effect on bath stability. The quality of the leveler in an acid copper plating chemistry determines the quality of copper pillars, under bump metallurgy (UBM), redistribution lines (RDLs) as well as its ability to fill through silicon vias (TSVs). Most of the MEMs, LED, and semiconductor customers require flat and smooth surfaces but there are some applications that require convex surfaces. The selection and optimization of electroplating conditions, especially the plating chemistry, play a key role in obtaining desired surface topographies. Many of the users of such plating chemistries are large semiconductor fabs, integrated device manufacturers (IDMs), or packaging houses who typically process semiconductor chips with different geometries, dimensions, including different heights. The fabs and packaging houses are making these semiconductor chips for fabless companies, IDMs and/or end users. Because the design of each and every one of these companies is different, this requires that the plating processes employed by the fabs and packaging houses are versatile and have a wide process window. For example, a fab makes semiconductor chips for fabless companies and IDMs. One of the steps is to electroplate copper pillars with via diameters ranging from about 10 μm to about 200 μm, and the height ranging from about 20 μm to about 150 μm. If the fab could use a single copper plating chemistry to meet all of its customer requirements on feature topography and within die uniformity, it would significantly reduce its manufacturing cost. If the fab uses multiple copper plating chemistries to cover the full range of the feature dimension, it would increase the manufacturing cost because it has to deal with not only a number of different chemistries, but also associated cost for product inventory, process control and maintenance, etc. Currently, in the market, there is no single commercial copper plating chemistry that could produce microchips with a wide range of feature dimensions at high yield, nor could a single commercial copper plating chemistry produce flat or convex topography by simply adjusting the concentration or composition. In addition, not a single commercial copper plating chemistry could produce same topography for features from about 10 um to about 150 um at deposition rate as high as 10 A/dm$^2$(ASD) or 5 um/min. A typical acid copper plating chemistry includes virgin makeup solution (VMS), which includes a metal salt, an acid, and chloride ion, and organic additives. The content of organic additives is typically very low (at ppm level) but they determine the surface features well as bulk properties of the electroplated layer. Organic additives can be categorized as a suppressor (or wetting agent), leveler (or grain refiner) and accelerator (or brightener). A suppressor acts as a wetting agent which helps to wet the metal surface so plating can take place. During deposition, it suppresses the growth rate of the deposited metal so it can grow by a layer by layer mechanism. Consequently, it results in adhesive, smooth metal surfaces without dendrites. A copper plating bath containing only a suppressor produces a matte or dull surface. To this composition, one can add a leveler. By definition, it levels or fills the "potholes" of the deposited surface in such a way that the height difference between the highest point and the lowest point of a given feature is minimized. In addition, a good leveler also ensures the height difference between the tallest and the shortest bump in a die is minimized. A copper plating bath contains both a suppressor and a leveler produces a surface that is somewhat reflective but not bright. To this composition, one can add an accelerator. By definition, it increases the copper deposition rate at the deposition potential. At the same time, it results in a reflective, shining surface. In semiconductor copper plating, the most critical component is the leveler, because ultimately it determines the within die uniformity, which largely determines the yield. Although choosing the right suppressor is also crucial, especially in the case of copper damascene, the core technology innovation today centers around the leveler for UBM, RDL, copper pillar and TSV plating. This is because taller features and larger dimensions are required for these applications (height 3 um to 100 um, line width 2 um to 20 um, diameter 10 to 100 um), therefore maintaining yield at >99.9% becomes extremely challenging. In addition, when taller copper pillar is required, it is critical to deposit copper at high deposition rate such as 10 ASD (5 um/min) or above so high productivity can be achieved. This allows the manufacturer to reduce the unit cost therefore to maintain its competitiveness. Clearly there is a need for versatile electrolytic copper deposition chemistry. As described below, the present invention offers such a solution by employing quaternary ammonium salts of dialkylaminoalkyl esters of 10-thiaxanthenecarboxylic acid and its derivatives as levelers. Although there are commercial copper plating baths that could meet one or more of the six challenges mentioned previously, there is none that could meet all six. The composition and method of present invention could as described below.

SUMMARY

In one aspect, a leveling composition comprises a compound of formula (I):

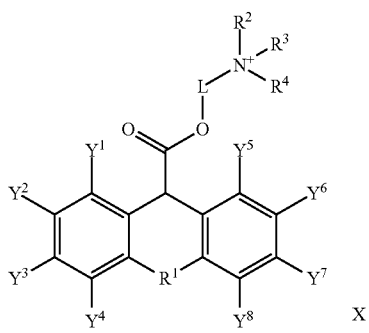

(I)

L, X, $R^1$, $R^2$, $R^3$, $R^4$, $Y^1$, $Y^2$, $Y^3$, $Y^4$, $Y^5$, $Y^6$, $Y^7$, and $Y^8$ are as defined below.

In another aspect, the compounds are of the formula (II):

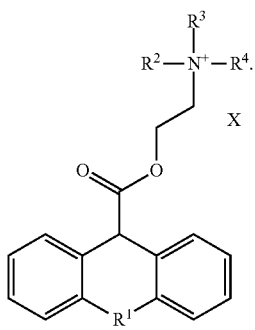

(II)

X, $R^1$, $R^2$, $R^3$, $R^4$, is defined as below.

In yet another aspect, a method for a metal onto a substrate comprises: contacting a substrate with an electrolytic metal deposition composition comprising a source of metal ions, and a leveler composition, wherein the leveler composition comprises the compound of formula (I); and applying an electrical current to the electrolytic deposition composition to deposit a metal onto the substrate.

DETAILED DESCRIPTION OF THE DISCLOSURE

Figure 1:
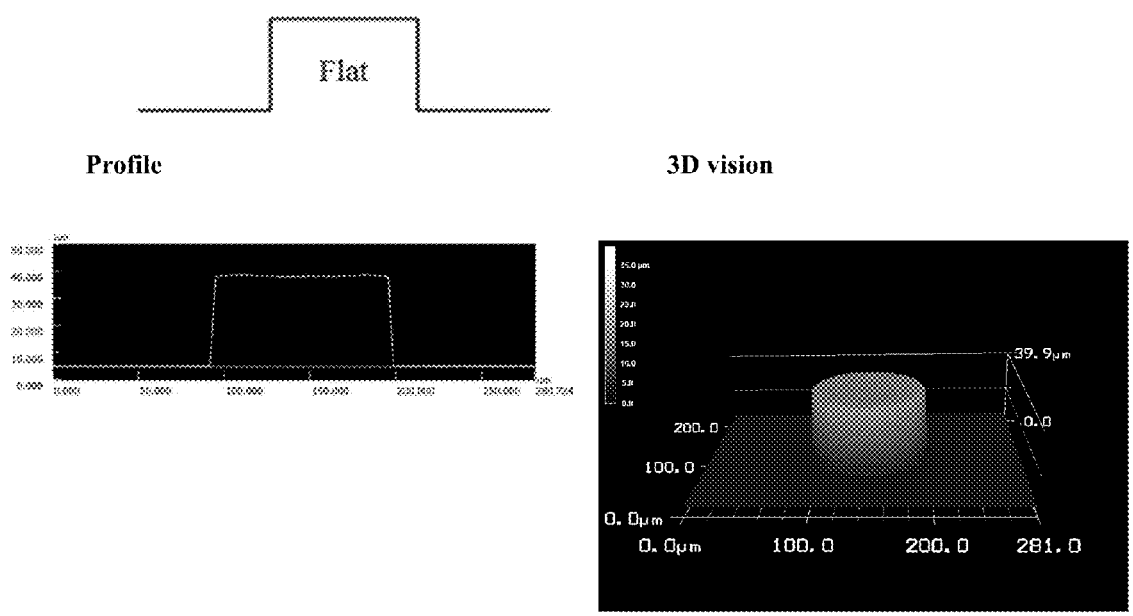
FIG. 1 is a copper pillar with a flat topography.
Figure 2:
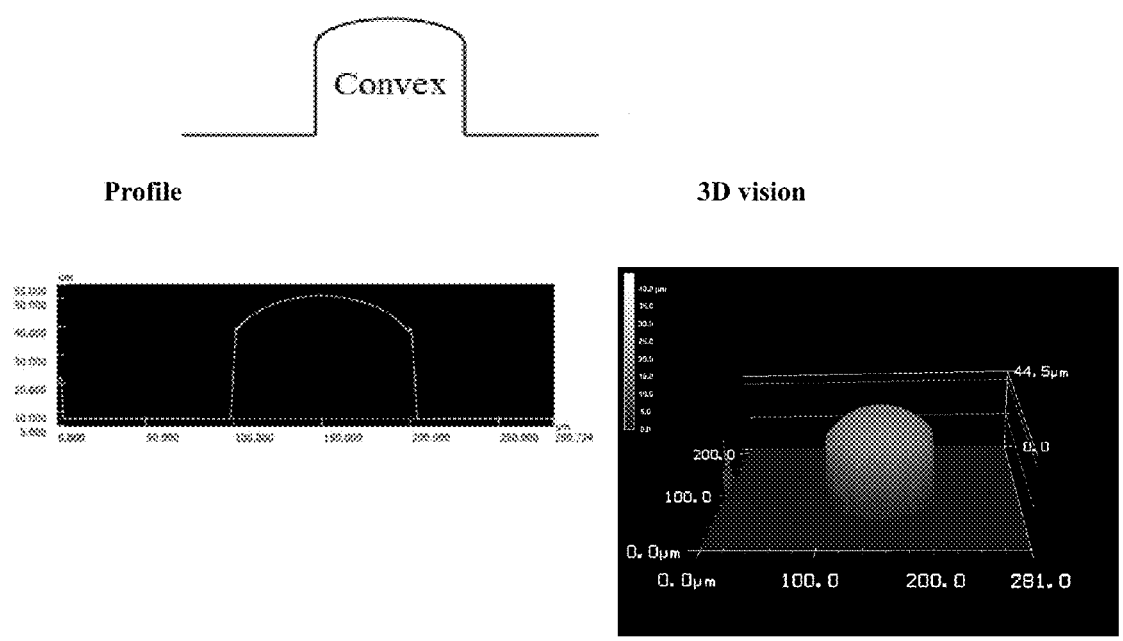
FIG. 2 is a copper pillar with a convex topography.
Figure 3:
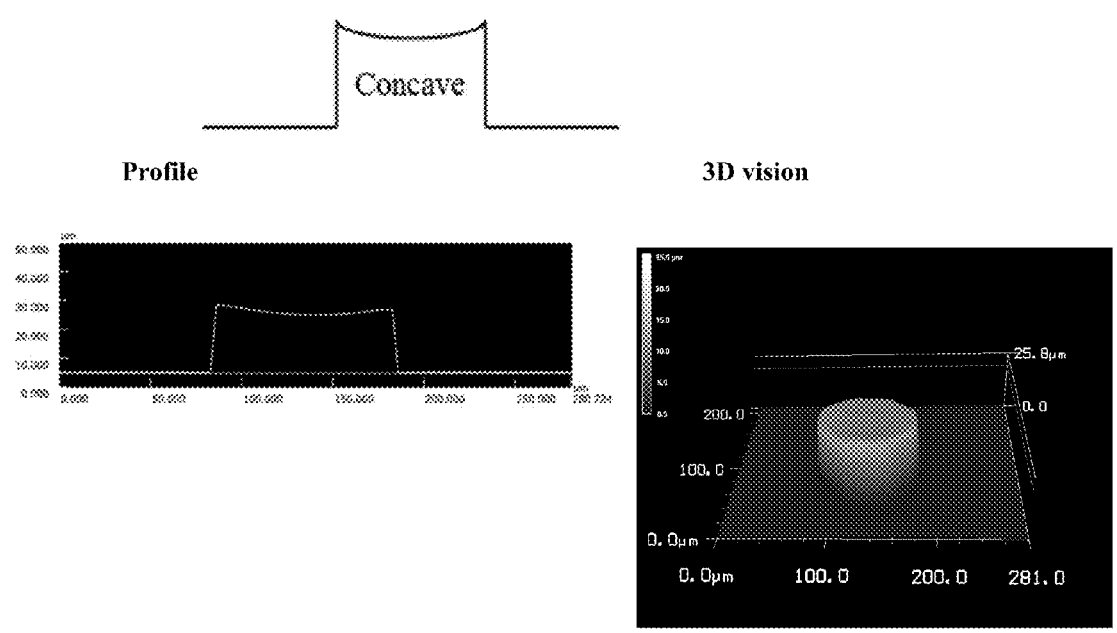
FIG. 3 is a copper pillar with a concave topography.

The present invention is directed to a composition and a method for electrodepositing of metal layers. In some preferred embodiments, the invention is directed to the composition and method for depositing copper or copper alloys. In some embodiments, the present invention is directed to a composition and a method for metalizing an interconnect feature in a semiconductor circuit device substrate, i.e., a wafer or die with desirable surface topography, good within die uniformity at high deposition rate. The semiconductor integrated circuit device substrate, i.e., a wafer or die, has a front surface and a back surface. The front surface is the surface on which integrated circuitry is built. Accordingly, the interconnect feature, i.e., a redistribution line or a copper pillar, is located on the front surface of the semiconductor substrate. The feature has an opening in the front surface of the substrate, a sidewall extending from the front surface of the substrate, and a bottom. The bottom is pre-deposited with a thin layer of copper seed layer. On a single die, features with same dimension or features with different dimensions can be found depending on customer design. In some cases, different features with different dimensions are built within a die. Needless to say, it is easier to realize copper deposition with same feature and same dimension than same feature but different dimensions on a die. During electroplating, the wafer is immersed into the plating bath, only the front surface where there are openings is conductive. When electrical connection is made between an anode and a cathode, both of which are immersed in the plating bath, electric circuitry is complete, and copper metallization by electrodeposition takes place. The quality of the plated surface is directly affected by the additives that are used in the plating bath.

Semiconductor substrates may comprise large sized (40 to 150 microns), low aspect ratio (0.3 to 1.25) via features, or small sized (10 nm to 30 microns), high aspect ratio (1.5 to 20) via features.

Semiconductor substrates may comprise lines with width ranging from 10 nm to 20 μm, length ranging from 20 nm to 200 μm.

These features may be located in a patterned dielectric film, the dielectric film is located on a semiconductor substrate. The semiconductor substrate may be, for example, a semiconductor wafer or chip. The semiconductor wafer is typically a silicon wafer or silicon chip, although other semiconductor materials, such as germanium, silicon germanium, silicon carbide, silicon germanium carbide, gallium nitride and gallium arsenide are applicable to the method of the present invention.

The semiconductor substrate has deposited thereon a dielectric film. The dielectric film is typically deposited on the semiconductor wafer or chip and then patterned by lithography, to achieve the circuitry pattern comprising the aforementioned redistribution lines, trenches, and vias.

In many logic, memory, power, and Radio Frequency (RF) devices, a smooth copper surface with flat topography is desirable. In other words, the copper surface should be shining, and flat from one end to another. This is especially true when the application is radio frequency. If the surface is rough, and/or surface topography is not flat, a percentage of the signal will be lost due to the so called skin effect, causing performance issues. In the case of copper pillar, especially if the subsequent interconnection is with another copper surface, it is critical that both surfaces are flat, otherwise the joint formed during the copper-copper bonding would not be strong enough to last during the product warrantee period. In some cases, a surface with slight convex shape maybe desirable. In most of the cases, a concave surface is undesirable for copper-copper bonding because no bond can be formed near the center of the feature. This would render the joint unreliable. Therefore, for copper pillar plating, it is important that the plating chemistries shall produce plated copper surface with slightly convex profile or preferably flat topography. As mentioned previously, the additive in an acid copper plating bath that controls the surface morphology is the leveler. Conventional levelers today can largely fulfill the role of producing slight convex surface. For some via dimensions, they can also produce flat topography. However, they are found not to be able to produce flat topography for ALL via dimensions AT THE SAME TIME when via diameters vary from about 10 microns to about 150 microns. One embodiment of the present invention is directed to a method of depositing bright copper pillars with flat topography with diameters ranging from about 10 microns to about 150 microns.

The method of the present invention comprises the incorporation of one of a particular class of leveler additives into the electrolytic copper plating chemistry. Plating chemistries containing these leveler additives produce excellent leveling effect over a wide range of feature aspect ratios and at high current densities. One embodiment of this method has been found to produce copper pillars and RDLs with flat topography for the dimensions described above. In addition, these leveler additives can produce copper pillars and RDLs with flat topography in one single bath composition. Furthermore, the copper pillars or RDLs with different sizes on a single die can be produced. In one embodiment, incorporation of one or more of this class of leveler additives with conventional leveler could produce copper pillar with any surface topography at will.

Definitions

When describing the compounds, compositions, methods and processes of this disclosure, the following terms have the following meanings, unless otherwise indicated.

The term "halogen" means a chlorine, bromine, iodine, or fluorine atom.

The term "alkyl" means a hydrocarbon group that may be linear, cyclic, or branched or a combination thereof having the number of carbon atoms designated (i.e., $C_{2-12}$ means two to twelve carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl groups include haloalkyl, thioalkyl, aminoalkyl, and the like.

The term "alkenyl" means a hydrocarbon group that contains at least one carbon-to-carbon double bond. Alkenyl groups can include, e.g., allyl, 1-butenyl, 2-hexenyl and 3-octenyl groups.

The term "alkynyl" means a hydrocarbon group that contains at least one carbon-to-carbon triple bond. Alkynyl groups can include, e.g., ethynyl, propargyl, and 3-hexynyl. Alkenyl and alkynyl groups can be substituted or unsubstituted, unless otherwise indicated.

The term "aryl" means a polyunsaturated, aromatic hydrocarbon group having 5-10 atoms and forming a single ring (monocyclic, preferably with 6 atoms such as phenyl) or multiple rings (bicyclic (preferably with 10 atoms such as naphthyl) or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "heteroaryl" means an aromatic group containing 5-10 atoms and at least one heteroatom (such as S, N, O, Si), where the heteroaryl group may be monocyclic (with preferably 5 or 6 atoms) or bicyclic (with preferably 9 or 10 atoms). Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "cycloalkyl" refers to saturated monocyclic, bicyclic, tricyclic, or other polycyclic hydrocarbon groups. Any atom can be substituted, e.g., by one or more substituents. A ring carbon serves as the point of attachment of a cycloalkyl group to another moiety. Cycloalkyl groups can contain fused rings. Fused rings are rings that share a common carbon atom. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "aralkyl" refers to an alkyl moiety in which an alkyl hydrogen atom is replaced by an aryl group. One of the carbons of the alkyl moiety serves as the point of attachment of the aralkyl group to another moiety. Aralkyl includes groups in which more than one hydrogen atom on an alkyl moiety has been replaced by an aryl group. Any ring or chain atom can be substituted e.g., by one or more substituents. Non-limiting examples of "aralkyl" include benzyl, 2-phenylethyl, 3-phenylpropyl, benzhydryl (diphenylmethyl), and trityl (triphenylmethyl) groups.

The term "heteroaralkyl" refers to an alkyl moiety in which an alkyl hydrogen atom is replaced by a heteroaryl group. One of the carbons of the alkyl moiety serves as the point of attachment of the aralkyl group to another moiety. Heteroaralkyl includes groups in which more than one hydrogen atom on an alkyl moiety has been replaced by a heteroaryl group. Any ring or chain atom can be substituted e.g., by one or more substituents. Heteroaralkyl can include, for example, 2-pyridylethyl.

The term "heterocyclyl" or "heterocyclic", which are synonymous as used herein, means a saturated or unsaturated non-aromatic ring containing at least 5-10 atoms (preferably 5 or 6) and at least one heteroatom (typically 1 to 5 heteroatoms) selected from nitrogen, oxygen or sulfur. The heterocyclyl ring may be monocyclic (with preferably 5 or 6 atoms) or bicyclic (with preferably 9 or 10 atoms). The ring system has 1-4 heteroatoms if monocyclic, 1-8 heteroatoms if bicyclic, or 1-10 heteroatoms if tricyclic, the heteroatoms selected from O, N, or S (and mono and dioxides thereof, e.g., N→O$^-$, S(O), SO$_2$). The heterocyclyl groups can contain fused rings. Fused rings are rings that share a common carbon atom. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "ring" means a compound whose atoms are arranged in formulas in a cyclic form. The ring compound can be either carbocyclic or heterocyclic.

The term "alkoxy" refers to an —O-alkyl radical. The term "mercapto" refers to an SH radical. The term "thioalkoxy" refers to an —S-alkyl radical. The terms "aryloxy" and "heteroaryloxy" refer to an —O-aryl radical and —O-heteroaryl radical, respectively. The terms "thioaryloxy" and "thioheteroaryloxy" refer to an —S-aryl radical and —S-heteroaryl radical, respectively.

The terms "aralkoxy" and "heteroaralkoxy" refer to an —O-aralkyl radical and —O-heteroaralkyl radical, respectively. The terms "thioaralkoxy" and "thioheteroaralkoxy" refer to an —S-aralkyl radical and —S-heteroaralkyl radical, respectively. The term "cycloalkoxy" refers to an —O-cycloalkyl radical. The terms "cycloalkenyloxy" and "heterocycloalkenyloxy" refer to an —O-cycloalkenyl radical and —O-heterocycloalkenyl radical, respectively. The term "heterocyclyloxy" refers to an —O-heterocyclyl radical. The term "thiocycloalkoxy" refers to an —S-cycloalkyl radical. The terms "thiocycloalkenyloxy" and "thioheterocycloalkenyloxy" refer to an —S-cycloalkenyl radical and —S-heterocycloalkenyl radical, respectively. The term "thioheterocyclyloxy" refers to an —S-heterocyclyl radical.

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be substituted e.g., by one or more substituents. The cycloalkenyl groups can contain fused rings. Fused rings are rings that share a common carbon atom. Cycloalkenyl moieties can include, e.g., cyclohexenyl, cyclohexadienyl, or norbornenyl.

The term "heterocycloalkenyl" refers to partially unsaturated monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, said heteroatoms selected from O, N, or S (and mono and dioxides thereof, e.g., N→O$^-$, S(O), SO$_2$) (e.g., carbon atoms and 1-4, 1-8, or 1-10 heteroatoms of N, O, or S if monocyclic, bicyclic, or tricyclic, respectively). A ring carbon (e.g., saturated or unsaturated) or heteroatom is the point of attachment of the heterocycloalkenyl substituent. Any atom can be substituted, e.g., by one or more substituents. The heterocycloalkenyl groups can contain fused rings. Fused rings are rings that share a common carbon atom. Heterocycloalkenyl groups can include, e.g., tetrahydropyridyl, dihydropyranyl, 4,5-dihydrooxazolyl, 4,5-dihydro-1H-imidazolyl, 1,2,5,6-tetrahydro-pyrimidinyl, and 5,6-dihydro-2H-[1,3]oxazinyl.

The term "substituent" refers to a group "substituted" on, e.g., an alkyl, cycloalkyl, alkenyl, alkynyl, aralkyl, heteroaralkyl, heterocyclyl, heterocycloalkenyl, cycloalkenyl, aryl, heteroaryl, arylcycloalkyl, heteroarylcycloalkyl, arylcycloalkenyl, heteroarylcycloalkenyl, arylheterocyclyl, heteroarylheterocyclyl, arylheterocycloalkenyl, or heteroarylheterocycloalkenyl group at any atom of that group. In one aspect, the substituent(s) (e.g., R$^a$) on a group are independently any one single, or any combination of two or more of the permissible atoms or groups of atoms delineated for that substituent. In another aspect, a substituent may itself be substituted with any one of the above substituents (e.g., R$^6$).

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

All of the above terms (e.g., "alkyl," "aryl," "heteroaryl" etc.), in some embodiments, include both substituted and unsubstituted forms of the indicated groups. These groups may be substituted multiple times, as chemically allowed.

The term "composition" as used herein is intended to encompass a product comprising the specified ingredients in the specified amounts, as well as any product which results, directly or indirectly, from combination of the specified ingredients in the specified amounts.

Compositions

A leveling composition comprises a compound of formula (I):

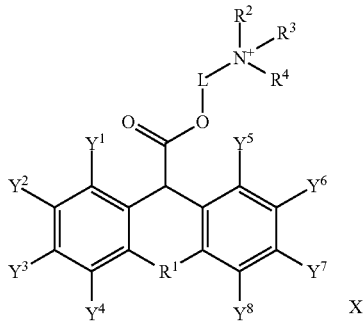

(I)

The anion X can be any suitable anion. In some embodiments, X are anions from organic acid, such as acetate, formate, oxalate, or cyanide. In some embodiments, X is carbonate, bicarbonate, phosphate, sulfate, or nitrate. In some embodiments, X is a halogen anion, such as $F^-$, $Cl^-$, $Br^-$, or $I^-$. In some embodiments, X is $Cl^-$, or $Br^-$.

$R^1$ is O, S or N. In some embodiments, $R^1$ is O.

$R^2$, $R^3$ and $R_4$ are independently selected from the group consisting of hydrogen, unsubstituted or substituted alkyl, unsubstituted or substituted alkenyl, unsubstituted or substituted alkynyl, unsubstituted or substituted $C_{3-12}$cycloalkyl, unsubstituted or substituted $C_{6-12}$ aryl, unsubstituted or substituted 3-12 membered heterocyclic, and unsubstituted or substituted 5-12 membered heteroaryl; or $R^2$ and $R^3$ may combine with an atom or atoms to which they are attached to form unsubstituted or substituted $C_{3-12}$cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, $R^2$, $R^3$ and $R^4$ are each independently unsubstituted or substituted alkyl. In some embodiments, $R^2$, $R^3$ and $R^4$ are each independently $C_{1-6}$alkyl. In some embodiments, $R^2$, $R^3$ and $R^4$ are independently selected from the group consisting of methyl, ethyl, propyl, and butyl. In some embodiments, $R^2$, $R^3$ and $R^4$ are independently selected from the group consisting of methyl, ethyl and isopropyl. In one embodiment, $R^2$ is methyl, and $R^3$ and $R^4$ are isopropyl. In one embodiment, $R^2$ and $R^3$ are ethyl. In one embodiment, $R^4$ is benzyl.

$Y^1$, $Y^2$, $Y^3$, $Y^4$, $Y^5$, $Y^6$, $Y^7$, and $Y^8$ are independently selected for the group consisting of hydrogen, halogen, unsubstituted or substituted alkyl, unsubstituted or substituted alkenyl, unsubstituted or substituted alkynyl, unsubstituted or substituted $C_{3-12}$cycloalkyl, unsubstituted or substituted $C_{6-12}$ aryl, unsubstituted or substituted 3-12 membered heterocyclic, and unsubstituted or substituted 5-12 membered heteroaryl.

In some embodiments, $Y^1$, $Y^2$, $Y^3$, $Y^4$, $Y^5$, $Y^6$, $Y^7$, and $Y^8$ are each independently unsubstituted or substituted alkyl. In some embodiments, $R^2$, $R^3$ and $R^4$ are each independently $C_{1-3}$ alkyl. In some embodiments, $Y^1$, $Y^2$, $Y^3$, $Y^4$, $Y^5$, $Y^6$, $Y^7$, and $Y^8$ are hydrogen. In some embodiments, at least one of $Y^1$, $Y^2$, $Y^3$, $Y^4$, $Y^5$, $Y^6$, $Y^7$, and $Y^8$ is halogen.

L is selected from the group consisting of unsubstituted or substituted alkyl, unsubstituted or substituted $C_{6-12}$ aryl, and unsubstituted or substituted 3- to 12-membered heterocyclyl. In some embodiments, L is $-(CH_2)_m-$. m is an Integer. In some embodiments, m is one or two.

In one embodiment, the leveling composition comprises a compound of formula (II):

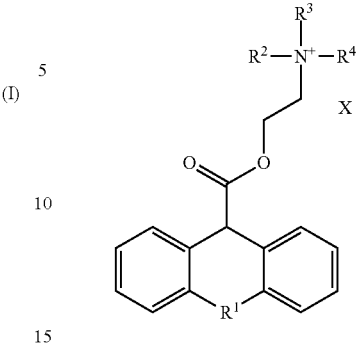

(II)

$R^1$ is O, S or N. In some embodiments, $R^1$ is O.

$R^2$, $R^3$ and $R^4$ are independently selected from the group consisting of hydrogen, unsubstituted or substituted alkyl, unsubstituted or substituted alkenyl, unsubstituted or substituted alkynyl, unsubstituted or substituted $C_{3-12}$ cycloalkyl, unsubstituted or substituted $C_{6-12}$ aryl, unsubstituted or substituted 3-12 membered heterocyclic, and unsubstituted or substituted 5-12 membered heteroaryl; or $R^2$ and $R^3$ may combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, $R^2$, $R^3$ and $R^4$ are each independently unsubstituted or substituted alkyl. In some embodiments, $R^2$, $R^3$ and $R^4$ are each independently $C_{1-6}$alkyl. In some embodiments, $R^2$, $R^3$ and $R^4$ are independently selected from the group consisting of methyl, ethyl, propyl, and butyl. In some embodiments, $R^2$, $R^3$ and $R^4$ are independently selected from the group consisting of methyl, ethyl and isopropyl. In one embodiment, $R^2$ is methyl, and $R^3$ and $R^4$ are isopropyl. In one embodiment, $R^2$ and $R^3$ are ethyl. In one embodiment, $R^4$ is benzyl.

A compound is of formula (III):

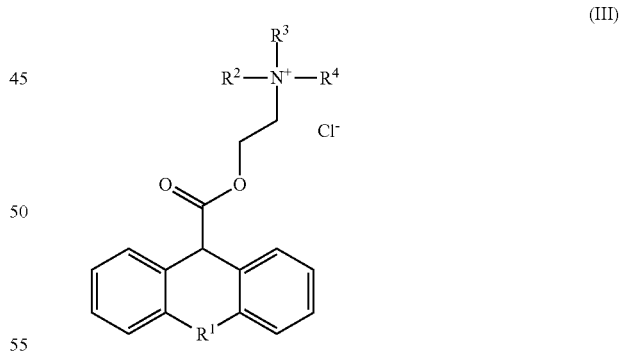

(III)

$R^1$ is O, S or N. In some embodiments, $R^1$ is O.

$R^2$, $R^3$ and $R^4$ are independently selected from the group consisting of hydrogen, unsubstituted or substituted alkyl, unsubstituted or substituted alkenyl, unsubstituted or substituted alkynyl, unsubstituted or substituted $C_{3-12}$ cycloalkyl, unsubstituted or substituted $C_{6-12}$ aryl, unsubstituted or substituted 3-12 membered heterocyclic, and unsubstituted or substituted 5-12 membered heteroaryl; or $R^2$ and $R^3$ may combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, $R^2$, $R^3$ and $R^4$ are each independently unsubstituted or substituted alkyl. In some embodiments, $R^2$, $R^3$ and $R^4$ are each independently $C_{1-6}$alkyl. In some embodiments, $R^2$, $R^3$ and $R^4$ are independently selected from the group consisting of methyl, ethyl, propyl, and butyl. In some embodiments, $R^2$, $R^3$ and $R^4$ are independently selected from the group consisting of methyl, ethyl and isopropyl. In one embodiment, $R^2$ is methyl, and $R^3$ and $R^4$ are isopropyl. In one embodiment, $R^2$ and $R^3$ are ethyl. In one embodiment, $R^4$ is benzyl.

The described leveler is an organic ammonium salt and possess relatively large conjugated system like aromatic rings on its side chains. The molecular weight of these levelers is in the range from ca. 300 to ca. 3000.

An exemplary leveler compound is L113, the structure of which is

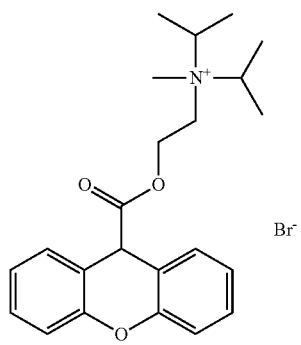 [SMILES: CC(C)[N+](C)(CCOC(=O)C1c2ccccc2Oc2ccccc21)C(C)C ; [Br-]]

Another exemplary leveler molecule is L117, the structure of which is

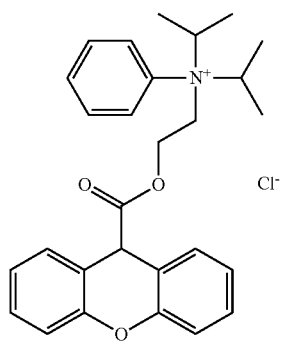 [SMILES: CC(C)[N+](CCOC(=O)C1c2ccccc2Oc2ccccc21)(c1ccccc1)C(C)C ; [Cl-]]

The present invention is directed to the composition of a new class of effective leveler additives in metal plating, particularly, in acid copper plating.

The present invention is also directed to a method of applying the said compounds in acid copper plating chemistries to electrodeposit copper traces and lines (RDLs) and copper pillars with good surface morphology and good within die uniformity.

In one embodiment, the said leveler in combination with an accelerator, a suppressor, and a VMS, produces copper pillars with different surface morphology by simply varying the concentration of the said leveler in the plating solution.

In yet another embodiment, the said leveler in combination with an accelerator, a suppressor, and a VMS, produces copper pillars with completely flat topography over a wide range of feature sizes (eg, diameters from 10 to 100 microns)

In yet another embodiment, the said leveler in combination with another leveler, an accelerator, a suppressor, and a VMS, produces copper pillars with different surface morphologies by varying the concentrations of the two levelers in the plating solution.

In yet another embodiment, the said leveler in combination with another leveler, an accelerator, a suppressor, and a VMS, produces copper pillars with flat topography, good within die uniformity with microbumps (definition: bump diameter<20 microns).

A wide variety of leveler compounds may be prepared from the reaction of xanthene-9-carboxylate or its derivatives having general structures (Ia) and aryl chlorinate having the general structures of (Ib). Reactions to prepare the leveler compounds may occur according to the conditions described in U.S. Pat. No. 2,659,732.

The compound has formula (Ia):

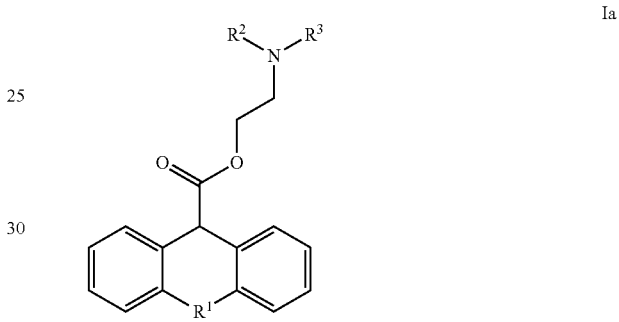

$R^1$, $R^2$, and $R^3$ are defined as above.
Another compound has formula (Ib):

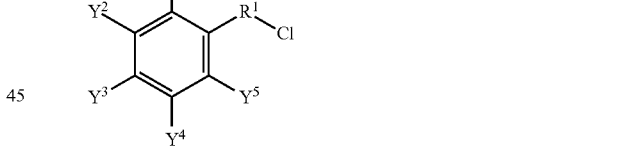

$R^1$, $Y^1$, $Y^2$, $Y^3$, $Y^4$, and $Y^5$ are defined as above.

In some embodiments, the leveler compound has formula (III), and the leveler may be prepared by selecting reaction conditions, i.e. temperature, concentration, etc., wherein the repeat units of the polymer comprise one moiety derived from formula (I).

The leveler compound may be added to the electrolytic copper deposition chemistry at a concentration between 0.1 mg/L to 400 mg/L, preferably from about 1 mg/L to about 80 mg/L, more preferably from 2 mg/L to about 30 mg/L. The levelers are typically prepared by adding other minor ingredients (as masking agents, in less than 100 mg/L), and then diluted with high purity water. A portion of this leveler solution is then added to the electrolytic copper plating composition in the concentrations indicated above. Advantageously, electrolytic copper plating compositions have been discovered to be tolerant to relatively higher concentrations of the leveler concentrations of the leveler compounds of the present invention compared to conventional leveler compounds. That is, an electrolytic copper plating composition may be tolerant to higher concentrations of the leveler compounds of the presentation invention without negatively impacting the copper deposition quality, i.e., surface morphology and deposition rate.

The electrolytic copper deposition chemistry of the present invention additionally comprises a source of copper ions, chloride ions, an acid, an accelerator, and a suppressor. The composition may comprise other materials that have other deposit properties, such as wetters, grain refiners, secondary brighteners, carriers, levelers and the like. In embodiments wherein an alloy is to be deposited, the electrolytic copper deposition chemistry further comprises a source of metal ions of the alloying metal that may be selected from among a source of tin ions, a source of silver ions, a source of zinc ions, a source of manganese ions, a source of zirconium ions, a source of bismuth ions, or a source of transition or refractory metal ions.

In embodiments wherein the metal or metals to be electrolytically deposited does not include copper, the deposition chemistry of the present invention additionally comprises a source of ions of the metal or metals to be deposited, such as a source of tin ions, a source of silver ions, a source of zinc ions, a source of manganese ions, a source of zirconium ions, a source of bismuth ions, or a source of transition or refractory metal ions, an acid, an accelerator, and a suppressor.

The accelerator and suppressor work together in a manner that advantageously enhances plating performance in conformal plating and surface appearance. Conformal plating is characterized by a deposit of equal thickness at all points of a feature (therefore flat). Conformal plating results from relatively equal copper deposition suppression across the entire feature surface and across the entire die. This could only be achieved with a superior leveling agent such as the ones in the present invention.

The accelerator may include an organic sulfur compound. Organic sulfur compounds currently preferred by the applicants are water soluble organic divalent sulfur compounds. In one preferred embodiment, the organic sulfur compound has the following general formula (IV):

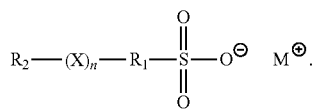
(IV)

Wherein X is O or S, preferably S;
n is 1 to 6;
M is hydrogen, alkali metal, or ammonium as needed to satisfy the valence;
$R_1$ is an alkylene or cyclic alkylene group of 1 to 8 carbon atoms, an aromatic hydrocarbon of 6 to 12 carbon atoms; and
$R_2$ is selected from the group of $MO_3SR_1$ wherein M and $R_1$ are as described above.

A preferred organic sulfur compound of formula (IV) has the following general formula (V), wherein M is a counter ion possessing sufficient positive charge to balance the negative charge on the oxygen atoms. M may be, for example, protons, alkali metal ions such as sodium and potassium, or another charge balancing cation such as ammonium or a quaternary amine.

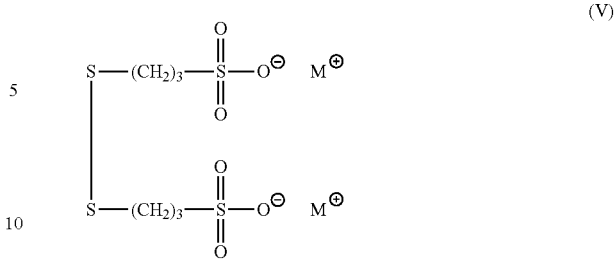
(V)

One example of the organic sulfur compound of formula (V) is the sodium salt of 3,3'-dithiobis(1-propane-sulfonate), which has the following formula (VI):

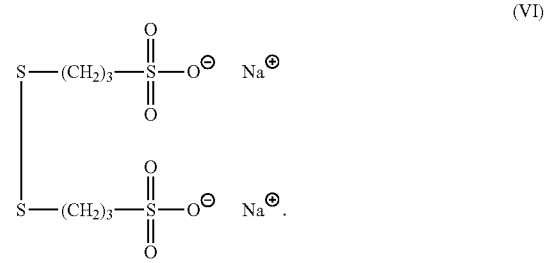
(VI)

An especially preferred example of the organic sulfur compound of formula (VII) is 3,3'-dithiobis(1-propane-sulfonic acid), which has the following formula (VII):

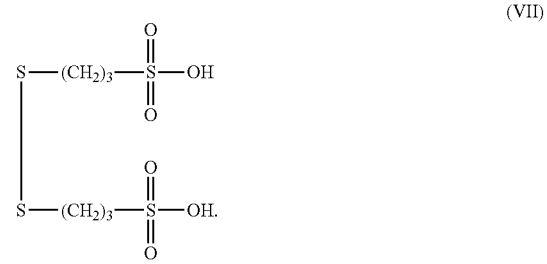
(VII)

The organic sulfur compound may be added in concentration between about 1 mg/L to about 50 mg/L, (ppm), preferably between about 3 mg/L to 30 mg/L, such as between about 15 mg/L and 25 mg/L. In a preferred embodiment, the organic sulfur compound is 3,3'dithiobis(1-propanesulfonic acid) added in a concentration of about 20 mg/L.

Suppressors typically comprise a polyether group covalently bonded to a base moiety. One class of applicable suppressors comprises a polymer group covalently bonded to an alcohol initiating moiety. With regard to suppressors comprising a polyether group covalently bonded to an initiating moiety comprising an ether group derived from an alcohol initiating moiety, the suppressor comprises at least two distinct ether functional groups; (1) an ether group derived from a reaction between alcohol and a random glycol unit or the polyether chain, and (2) ether groups derived from reactions between random glycol units within the polyether chain.

In those embodiments where the polyether chain comprises an initiating moiety comprising ether group derived from an alcohol, suitable alcohols include substituted or unsubstituted acyclic alcohols and substituted or unsubstituted cyclic alcohols. The alcohol comprises at least one hydroxyl group, and thus can be an alcohol or a polyol, the polyol comprising two or more hydroxyl groups such as between about two hydroxyl groups to about six hydroxyl groups. Acyclic alcohols comprise a substituted or unsubstituted alkyl, preferably a short chain hydrocarbon having between one and about twelve carbons, more preferably between about four and about ten carbons, which may be branched or straight chained. Exemplary acyclic alcohols include n-butanol, iso-butanol, tert-butanol, pentanol, neo-pentanol, tert-army alcohol, ethylene glycol, 1,2-butanediol, 1,3-butandio 1,1,4-butandiol, and glycercol, among others. Cycloalkyl groups typically have a 5- to 7-carbon ring, although bicylic, tricylic, and higher multi-cyclic alkyl groups are applicable.

The polyether comprises a chain of random glycol units wherein the chain of random glycol units can be formed by the polymerization of epoxide monomers. Preferably, the polyether comprises a chain of random glycol units formed by the polymerization of both ethylene oxide monomer and propylene oxide monomer. The ratio of ethylene oxide (EO) glycol units and propylene oxide (PO) glycol units in the polyether can be between about 1:9 to about 9:1. In some embodiments, the ratio is between about 1:3 to about 3:1, such as about 1:1. The random polyether can comprise up to about 800 EO glycol units and up to about 250 PO glycol units. In a preferred embodiment, the random polyether comprises between about 20 and about 25 EO glycol units and between about 15 and about 20 PO glycol units. The molecule weight of the random polyether can be as low as 500 g/mole and as high as about 50,000 g/mole, preferably between about 1000 g/mole to 20,000 g/mole, and more preferably between 1000 g/mole to 10,000 g/mole.

An exemplary suppressor compound comprising a polyether group covalently bonded to a moiety derived from an alcohol is shown in formula(VII)Formula VIII is a suppressor comprising a PO/EO random copolymer covalently bonded to a moiety derived from n-butanol having the structure

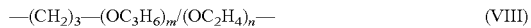

—(CH$_2$)$_3$—(OC$_3$H$_6$)$_m$/(OC$_2$H$_4$)$_n$—  (VIII)

Wherein n can be between 1 and about 200 and m can be between 1 and about 200. The number ratio of EO:PO units is such that the suppressor compound preferably comprises between about 45% and about 55% by weight EO units and between about 55% and 45% by weight PO units, the EO and PO units arranged randomly in the polyether chain. The molecular weight of the random PO/EO copolymer can be between about 2000 g/mole to about 20,000 g/mole, and preferably between about 1500 g/mole to about 4500 g/mole.

An exemplary suppressor compound having the formula VIII is available from Aladdin Chemistry Co. Ltd., under the trade designation Poly ethylene glycol.

Wide variety of electrolytic copper deposition chemistries are potentially applicable. The electrolytic baths include acid baths and alkaline baths, exemplary electrolytic copper plating baths include copper fluoroborate, copper pyrophosphate, copper cyanide, copper phosphate, copper sulfate, and other copper metal complexes such as copper methane sulfonate and copper hydroxylethylsulonate. Preferred copper sources include copper sulfate in sulfuric acid solution and copper methane sulfonate in methane sulfonic acid solution.

In embodiments wherein the copper source is copper sulfate and acid is sulfuric acid, the concentration of copper ion and acid may vary over wide limits; for example, from about 4 to 70 g/L copper and from about 2 to about 225 g/L sulfuric acid. In this regard the compounds of the invention are suitable for use in distinct acid/copper concentration ranges, such as high acid/low copper systems, in low acid/high copper systems, and mid acid/high copper systems. In high acid/low copper systems, the copper ion concentration can be on the order of 4 g/L to on the order of 30 g/L; and the acid concentration may be sulfuric acid in an amount greater than about 100 g/L up to 225 g/L. In an exemplary high acid low copper system, the copper ion concentration is about 17 g/L, where the sulfuric acid concentration is about 180 g/L. In some low acid/high copper systems, the copper ion concentration can be between 35 g/L to about 65 g/L, such as between 38 g/L and about 50 g/L. 35 g/L copper ion corresponds to about 140 g/L CuSO$_4$.5H$_2$O, copper sulfate pentahydrate. In some low acid high copper systems, the copper ion concentration can be between 30 to 60 g/L, such as between 40 g/L to about 50 g/L. The acid concentration in these systems is preferably less than about 100 g/L.

In other embodiments, the copper source is copper methanesulfonate and the acid is methanesulfonic acid. The use of copper mathanesulfonate as the copper source allows for greater concentrations of copper ions in the electrolytic copper deposition chemistries in comparison to other copper ion sources. Accordingly, the source of copper ion may be added to achieve copper ion concentrations greater than about 80 g/L, greater than about 90 g/L, or even greater than about 100 g/L, such as, for example about 110 g/L. Preferably, the copper methanesulfonate is added to achieve a copper ion concentration between about 30 g/L to about 100 g/L, such as between about 40 g/L and about 60 g/L. High copper concentrations enabled by the used of copper methanesulfonate is thought to be one method for alleviating the mass transfer problem, i.e., local depletion of copper ions particularly at the bottom of deep features. High copper concentrations in the bulk solution contribute to a step copper concentration gradient that enhances diffusion of copper into the features.

When copper methane sulfonate is used, it is preferred to use methane sulfonic acid for acid pH adjustment. This avoids the introduction of unnecessary anions into the electrolytic deposition chemistry. When methane sulfonic acid is added, its concentration may be between about 1 ml/L to about 400 ml/L.

Chloride ion may also be used in the bath at a level up to about 200 mg/L (about 200 ppm), preferably from about 10 mg/L to about 90 mg/L (about 10 to 90 ppm), such as about 50 mg/L (about 50 ppm). Chloride ion is added in these concentration ranges to enhance the function of other bath additives. In particular, it has been discovered that the addition of chloride ion enhances the effectiveness of a leveler. Chloride ions are added using HCl.

A source of alloying metal ions may be added to the composition to plate a copper alloy. Sources of alloying metal ions include a source of tin ions, a source of silver ions, a source of zinc ions, a source of manganese ions, a source of zirconium ions, a source of bismuth ions, or a source of transition or refractory metal ions. Typically, the sources of these alloying metal ions many be the same as the source of the copper ions. That is, if a copper sulfate is used as the copper source, it is preferred to use tin sulfate and zinc sulfate as the alloying metal ion sources. Alternatively, if copper methane sulfonate is used, the sources of tin ions and zinc ions are preferably methanesulfonate salts of these ions.

These are typically added in concentrations from 0.05 to about 25 g/L. The concentration may vary depending upon the desired alloy metal content in the deposited copper alloy.

A large variety of additives may typically be used in the bath to provide desired surface finishes and metallurgies for the plated copper metal. Usually more than one additive is used to achieve desired functions. At least two or three additives are generally used to initiate good copper deposition as well as to produce desirable surface morphology with good conformal plating characteristics. Additional additives (usually organic additives) include wetter, grain refiners and secondary brighteners and polarizers for the suppression of dendritic growth, improved uniformity and defect reduction.

Plating equipment for plating semiconductor substrates is well known and is described in, for example, Haydu et al. U.S. Pat. No. 6,024,856. Plating equipment comprises an electrolytic plating tank which holds copper electrolytic solution and which is made of a suitable material such as plastic or other material inert to the electrolytic plating solution. The tank may be cylindrical, especially for wafer plating. A cathode is horizontally disposed at the upper part of the tank and may be any type of substrate such as a silicon wafer having openings such as lines and vias. The wafer substrate is typically coated first with barrier layer, which may be titanium nitride, tantalum, tantalum nitride, or ruthenium to inhibit copper diffusion, and next with a seed layer of copper or other metal to initiate copper electrodeposition. A copper seed layer may be applied by chemical vapor deposition (CVD), physical vapor deposition (PVD), or the like. An anode is also preferably circular for wafer plating and is horizontally disposed at the lower part of tank forming a space between the anode and the cathode. The anode is typically a soluble anode such as copper metal.

The bath additives can be used in combination with membrane technology being developed by various plating tool manufacturers. In this system, the anode may be isolated from the organic bath additives by a membrane. The purpose of the separation of the anode and the organic bath additives is to minimize the oxidation of the organic bath additives on the anode surface.

The cathode substrate and anode are electrically connected by wiring and, respectively, to a rectifier (power supply). The cathode substrate for direct or pulse current has a net negative charge so that copper ions in the solution are reduced at the cathode substrate forming plated copper metal on the cathode surface. An oxidation reaction takes place at the anode. The cathode and anode may be horizontally or vertically disposed in the tank.

During operation of the electrolytic plating system, a pulse current, direct current, reverse periodic current, or other suitable current may be employed. The temperature of the electrolytic solution may be maintained using a heater/cooler whereby electrolytic solution is removed from the holding tank and flows through the heater/cooler and it is recycled to the holding tank.

Electrodeposition conditions such as applied voltage, current density, solution temperature, and flow condition are essentially the same as those in conventional electrolytic copper plating methods. For example, the bath temperature is typically about room temperatures such as about 20 to 27° C., but may be at elevated temperatures up to about 40° C., or higher. The electrical current density is typically from about 0.2 A/dm$^2$ to about 6 A/dm$^2$, but may also be up to about 20 A/dm$^2$, such as about 10 A/dm$^2$. It is preferred to use an anode to cathode ratio of 1:1, but this may also vary widely from about 1:4 to about 4:1. The process also uses mixing in the electrolytic plating tank which may be supplied by agitation or preferably by the circulating flow of recycle electrolytic solution through the tank.

Copper deposited from the electrolytic deposition chemistry of the present invention comprising the above described leveler compounds is of high purity and density, is of high smoothness and flat surface topography.

Having described the invention in detail, it will be apparent that modifications and variations are possible without departing from the scope of the invention defined in the appended claims.

EXAMPLES

The following non-limiting examples are provided to further illustrate the present invention. While the leveler of present invention can be used in electroplating of metals such as copper, tin, nickel, zinc, silver, gold, palladium, platinum, and iridium, only electrolytic copper plating chemistries are described below.

Figure 4:
FIG. 4 is a Hull cell panel of copper deposition at 3 A for 2 minutes in the presence of L113.

Example 1 (FIG. 4)

Electrolytic Copper Deposition Chemistry of the Invention

An electrolytic copper plating composition of the invention was prepared having the following components and concentrations
a. Copper ion from copper sulfate (50 g/L, Cu$^{2+}$)
b. Sulfuric acid (100 g/L)
c. Chloride ion (70 ppm)
d. L113 (30 ppm)

The electrolytic copper deposition chemistry was prepared according to the instructions of Table I. Plating conditions are summarized in Table II

TABLE I

| Bath composition | Components | Concentration | Unit | Preparation |
|---|---|---|---|---|
| VMS (500 ml) | CuSO4•5H2O | 200 | g/L | Calculated amount of CuSO4•5H2O is dissolved with double distilled water, calculated amount of H2SO4 and HCl was then added slowly, the solution is then filtered and diluted to 1 L. 500 mL of the prepared solution was transferred to a beaker for subsequent use. |
| | H2SO4 | 100 | g/L | |
| | Cl$^-$ | 80 | ppm | |
| Additives | Suppressor | 1000 | ppm | The additives in solid form are dissolved with double distilled water and diluted to 50 ml, calculated amount of suppressor, leveler, and accelerator products are then added to the plating bath and stirred at 500 rpm for 20~30 min. |
| | Leveler | calculated | ppm- | |
| | Accelerator | 10 | ppm | |

TABLE II

| | Hull Cell Plating Conditions | | |
|---|---|---|---|
| Target bump thickness (um) | Current (A) | Plating duration (min) | Agitation (rpm) |
| 5 | 3 | 2 | Air agitation |

Figure 5:
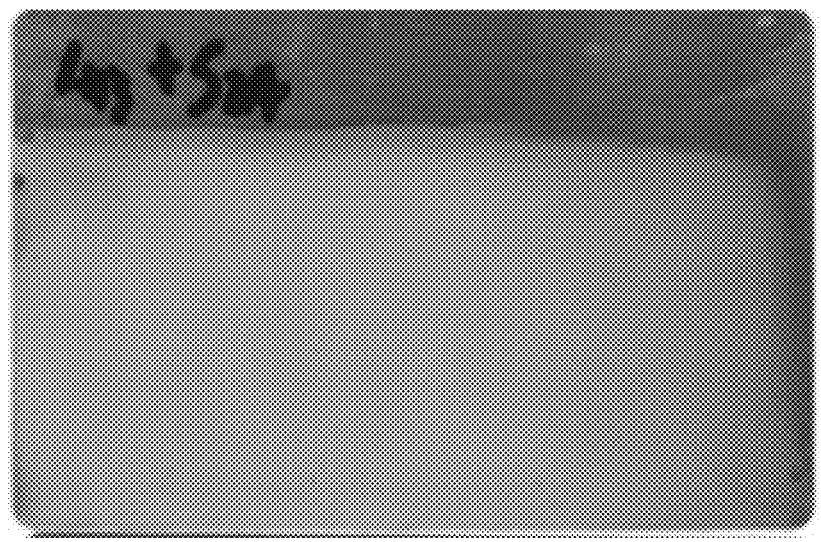
FIG. 5 is a Hull cell panel of copper deposition at 3 A for 2 minutes in the presence of L113 plus a suppressor, note the improvement of plating at low current density region. The panel is somewhat reflective but not bright.

Example 2 (FIG. 5)

Electrolytic Copper Deposition Chemistry of the Invention

An electrolytic copper plating composition of the invention was prepared having the following components and concentrations
   a. Copper ion from copper sulfate (50 g/L, $Cu^{2+}$)
   b. Sulfuric acid (100 g/L)
   c. Chloride ion (70 ppm)
   d. L113 (30 ppm)
   e. S24 (1000 ppm)

The electrolytic copper deposition chemistry was prepared according to the instructions of Table I. Plating conditions are summarized in Table II

Figure 6:
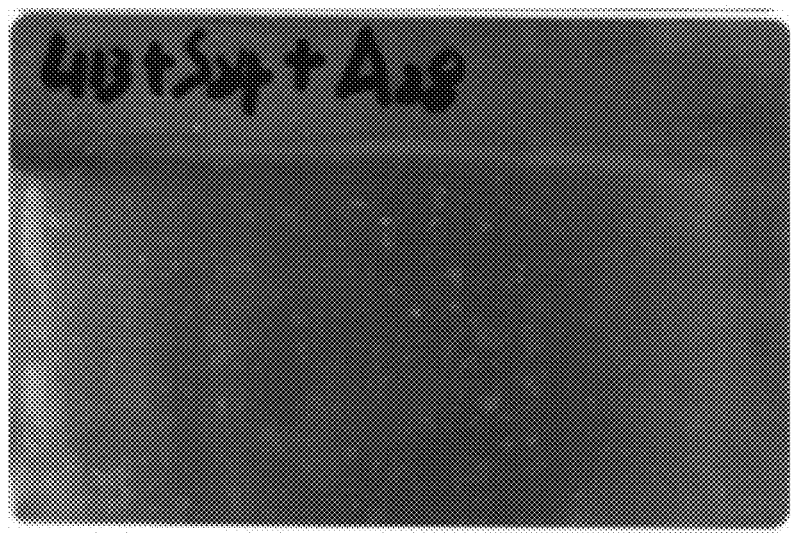
FIG. 6 is a Hull cell panel of copper deposition at 3 A for 2 minutes in the presence of L113 plus a suppressor and an accelerator, note the improvement of plating. The entire panel becomes reflective and bright.

Example 3 (FIG. 6)

Electrolytic Copper Deposition Chemistry of the Invention

An electrolytic copper plating composition of the invention was prepared having the following components and concentrations
   a. Copper ion from copper sulfate (50 g/L, $Cu^{2+}$)
   b. Sulfuric acid (100 g/L)
   c. Chloride ion (70 ppm)
   d. L113 (30 ppm)
   e. S24 (1000 ppm)
   f. A28 (10 ppm)

The electrolytic copper deposition chemistry was prepared according to the instructions of Table I. Plating conditions are summarized in Table II

Figure 7:
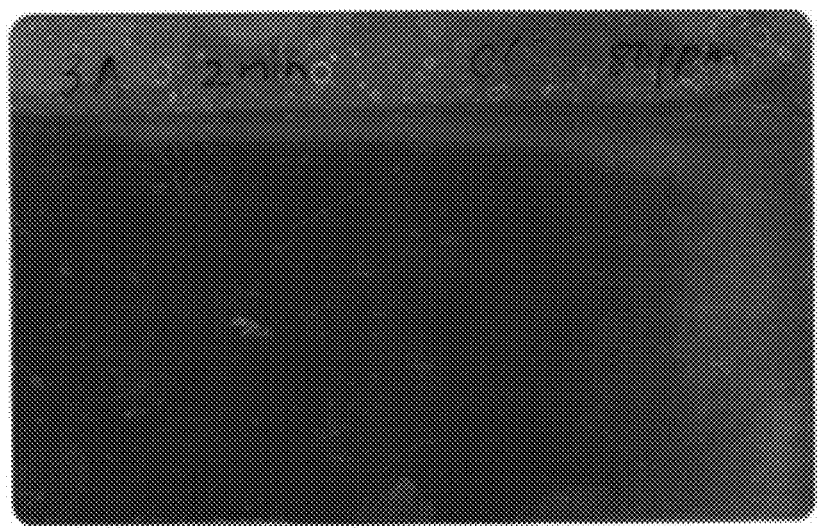
FIG. 7 is a Hull cell panel of copper deposition at 3 A for 2 minutes in the presence of L26 (a typical conventional leveler) plus a suppressor and an accelerator.
Figure 8:
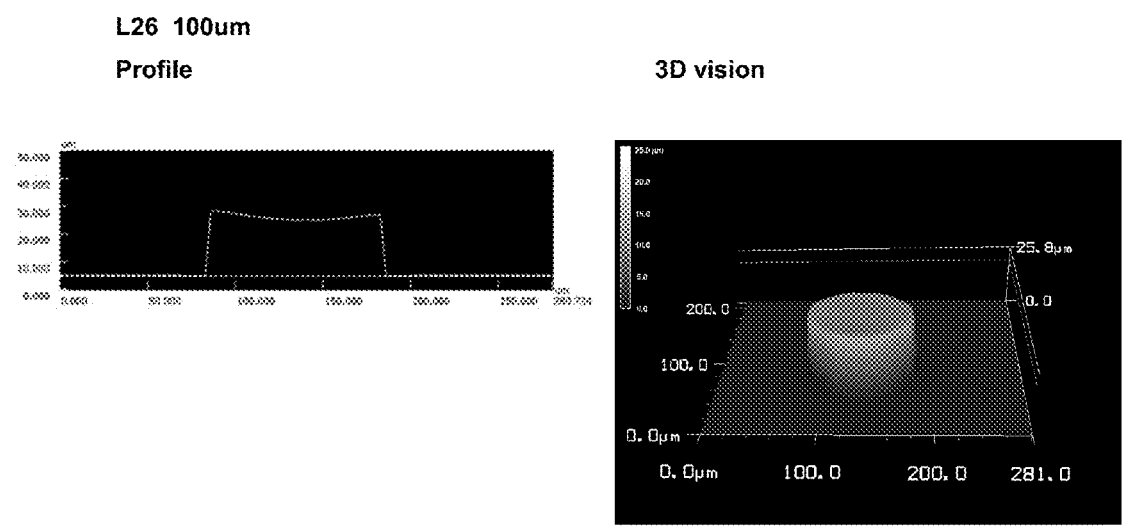
FIG. 8 is the 3D laser microscope imaging of a copper pillar with L26 as the leveler, pillar diameter=100 μm.
Figure 9:
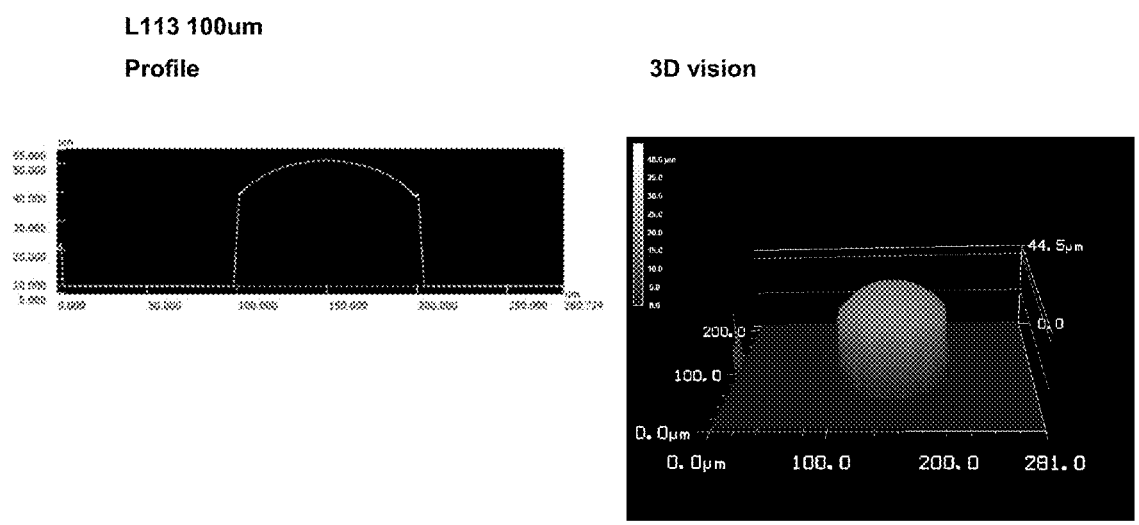
FIG. 9 is the 3D laser microscope imaging of a copper pillar with L113 as the leveler, pillar diameter=100 μm.
Figure 10:
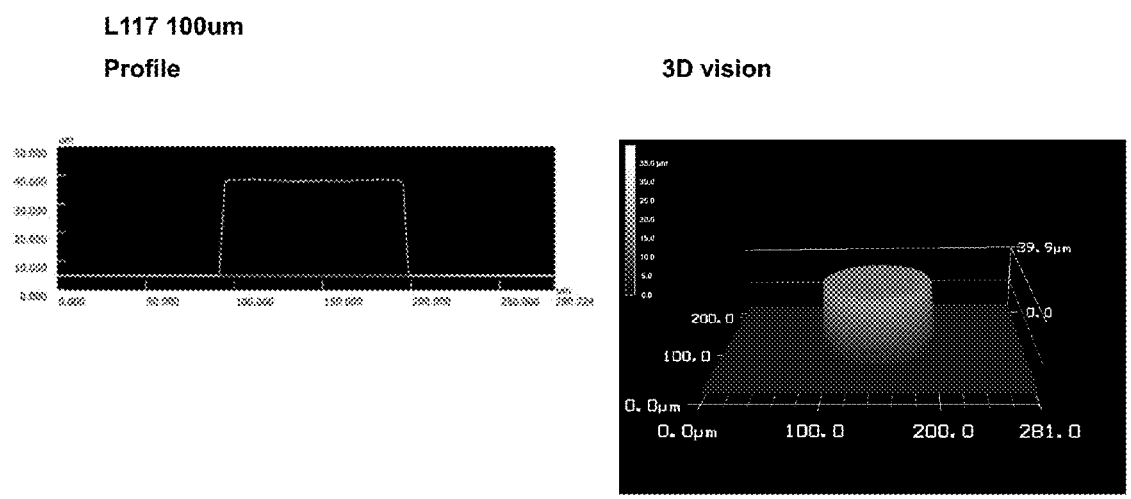
FIG. 10 is the 3D laser microscope imaging of a copper pillar with L117 as the leveler, pillar diameter=100 μm.
Figure 11:
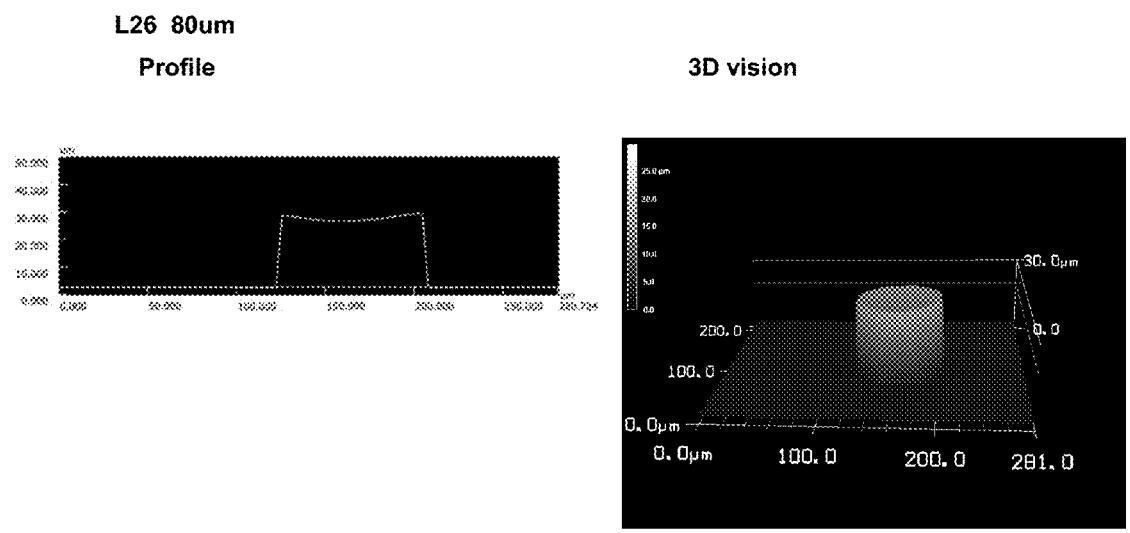
FIG. 11 is the 3D laser microscope imaging of a copper pillar with L26 as the leveler, pillar diameter=80 μm.
Figure 12:
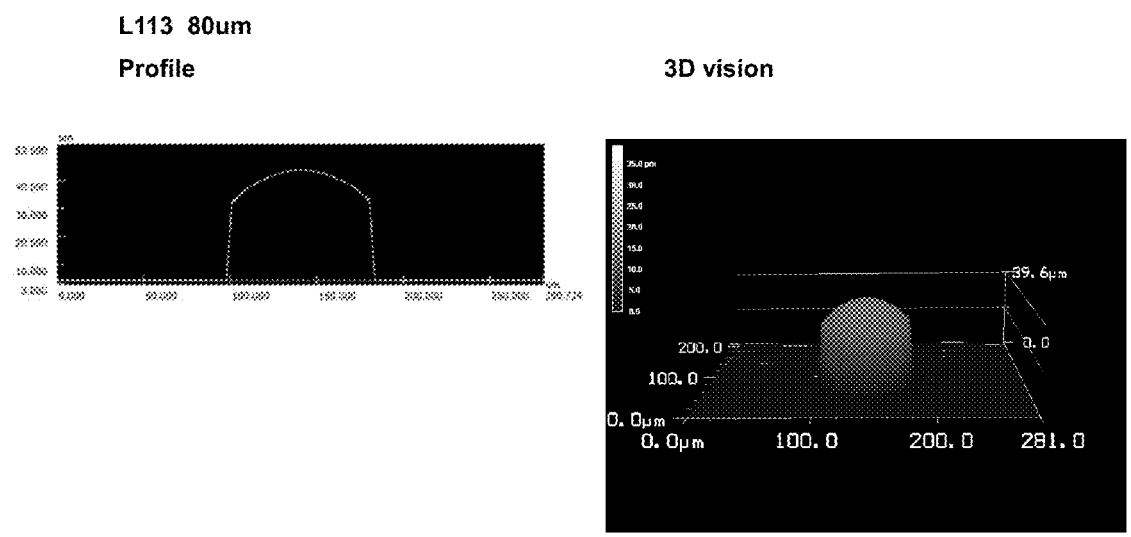
FIG. 12 is the 3D laser microscope imaging of a copper pillar with L113 as the leveler, pillar diameter=80 μm.
Figure 13:
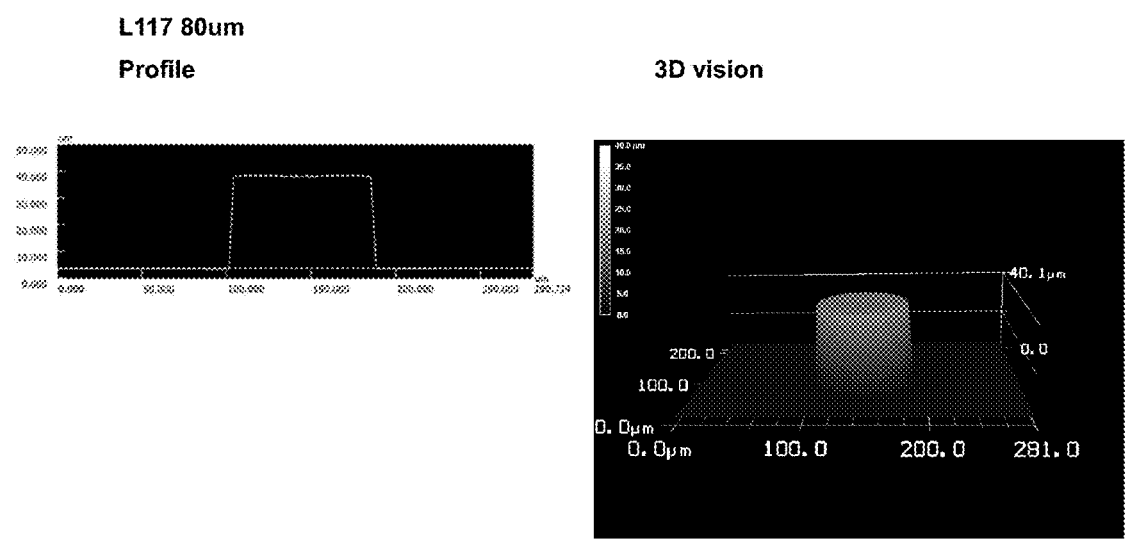
FIG. 13 is the 3D laser microscope imaging of a copper pillar with L117 as the leveler, pillar diameter=80 μm.
Figure 14:
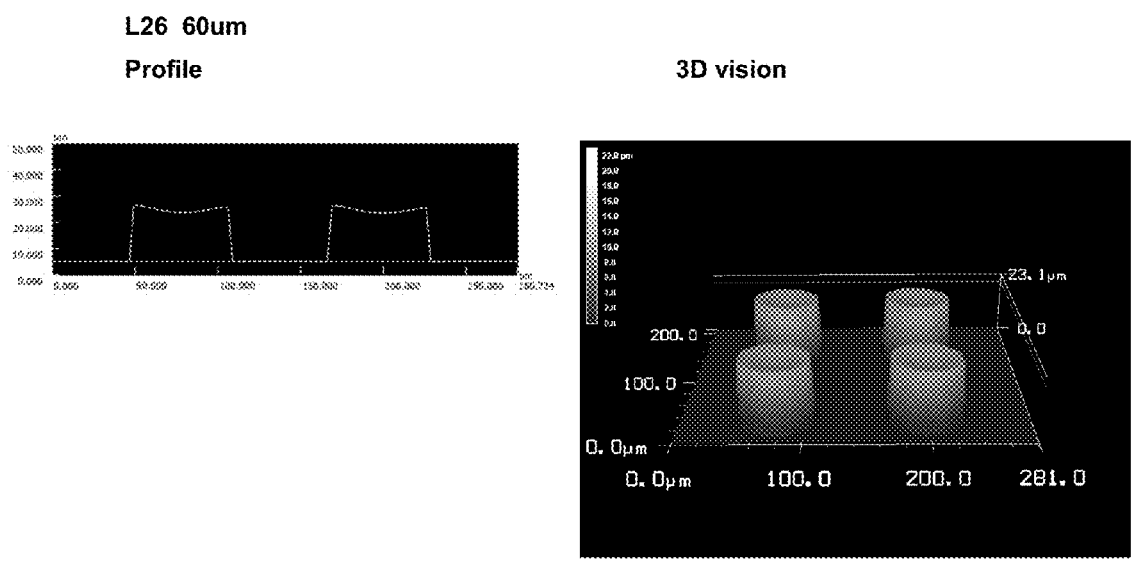
FIG. 14 is the 3D laser microscope imaging of a copper pillar with L26 as the leveler, pillar diameter=60 μm.
Figure 15:
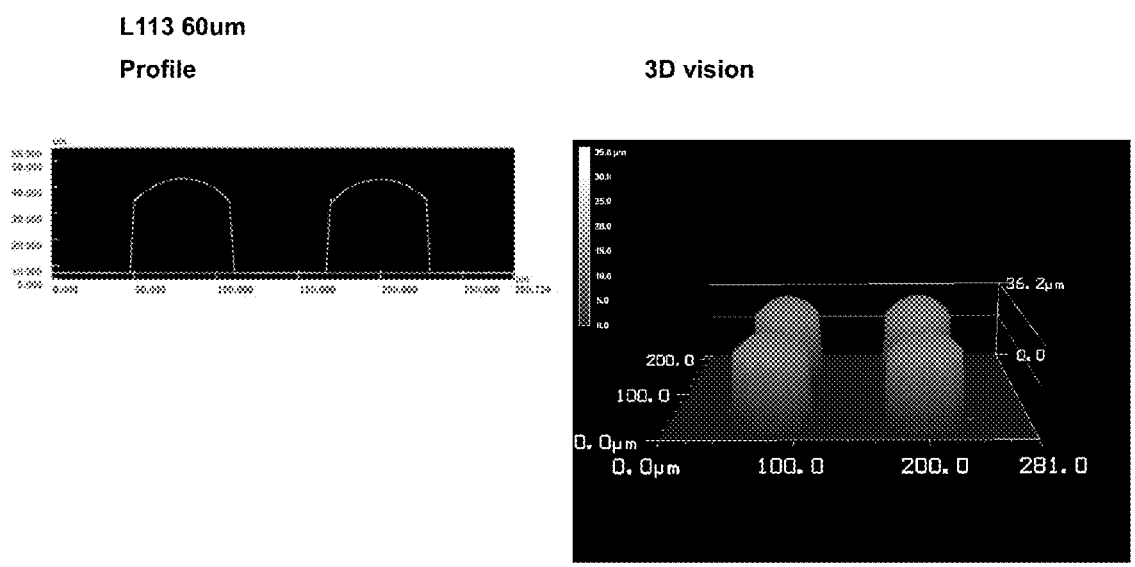
FIG. 15 is the 3D laser microscope imaging of a copper pillar with L113 as the leveler, pillar diameter=60 μm.
Figure 16:
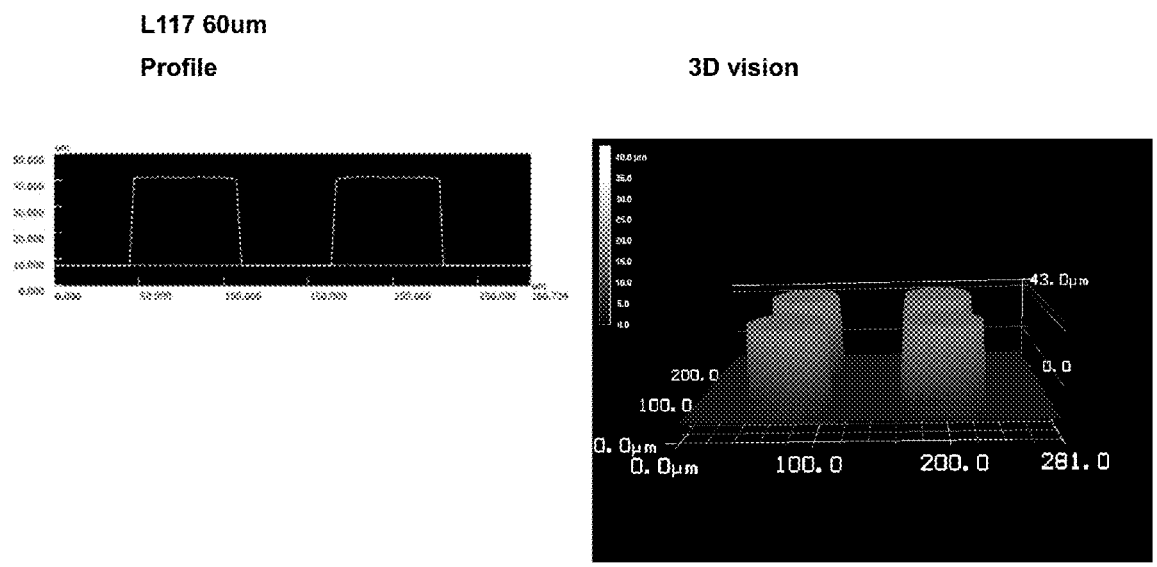
FIG. 16 is the 3D laser microscope imaging of a copper pillar with L117 as the leveler, pillar diameter=60 μm.
Figure 17:
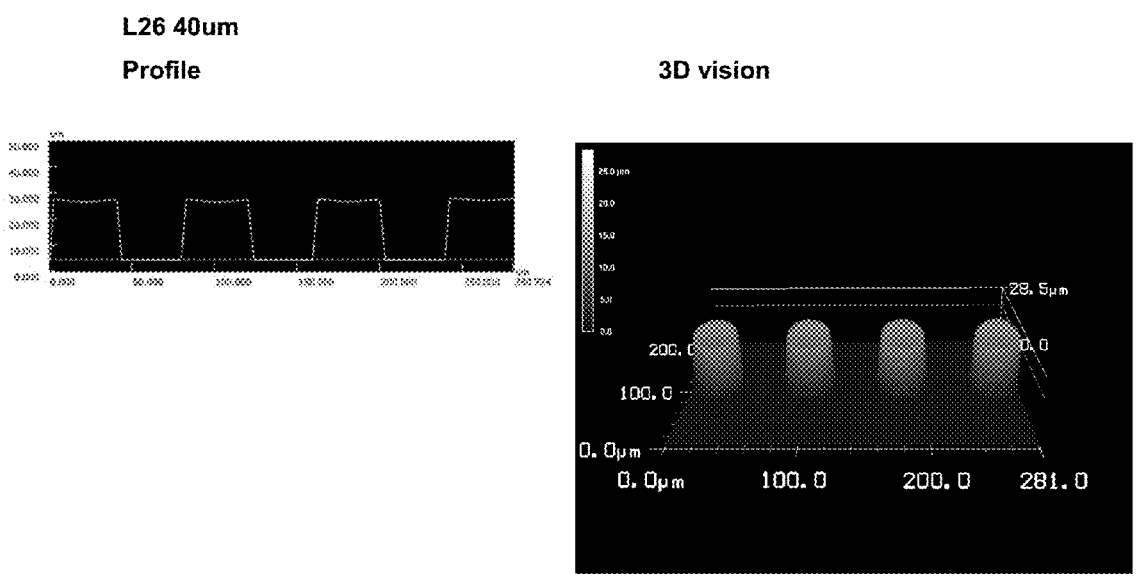
FIG. 17 is the 3D laser microscope imaging of a copper pillar with L26 as the leveler, pillar diameter=40 μm.
Figure 18:
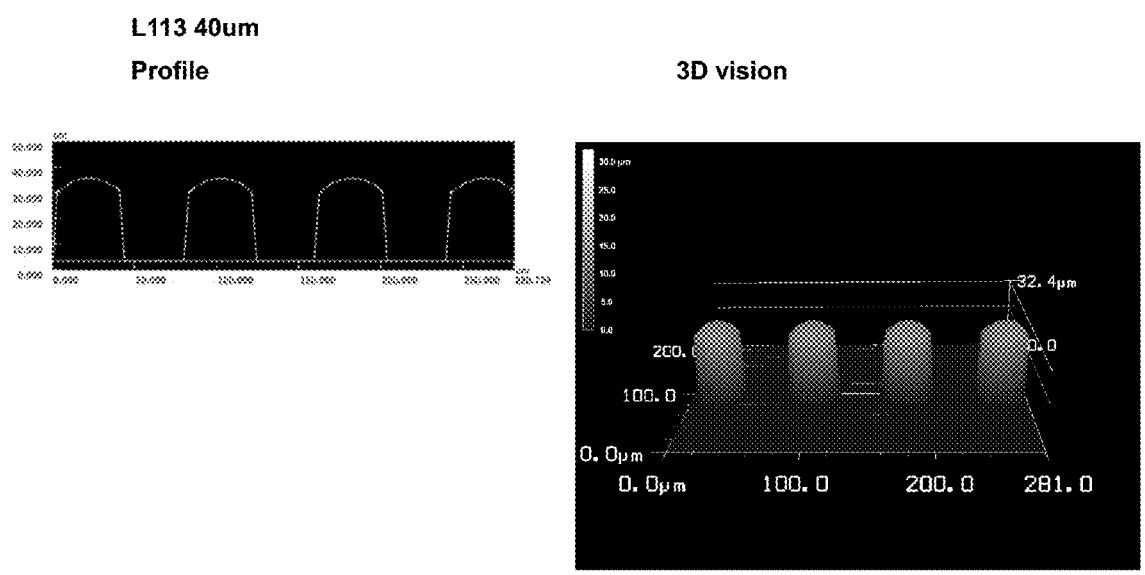
FIG. 18 is the 3D laser microscope imaging of a copper pillar with L113 as the leveler, pillar diameter=40 μm.
Figure 19:
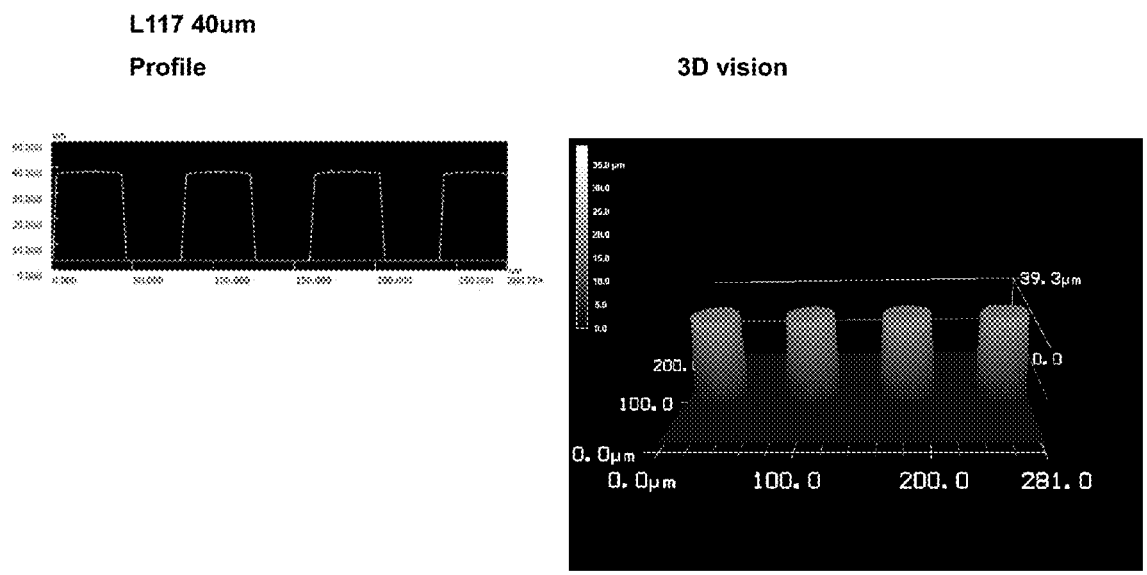
FIG. 19 is the 3D laser microscope imaging of a copper pillar with L117 as the leveler, pillar diameter=40 μm.
Figure 20:
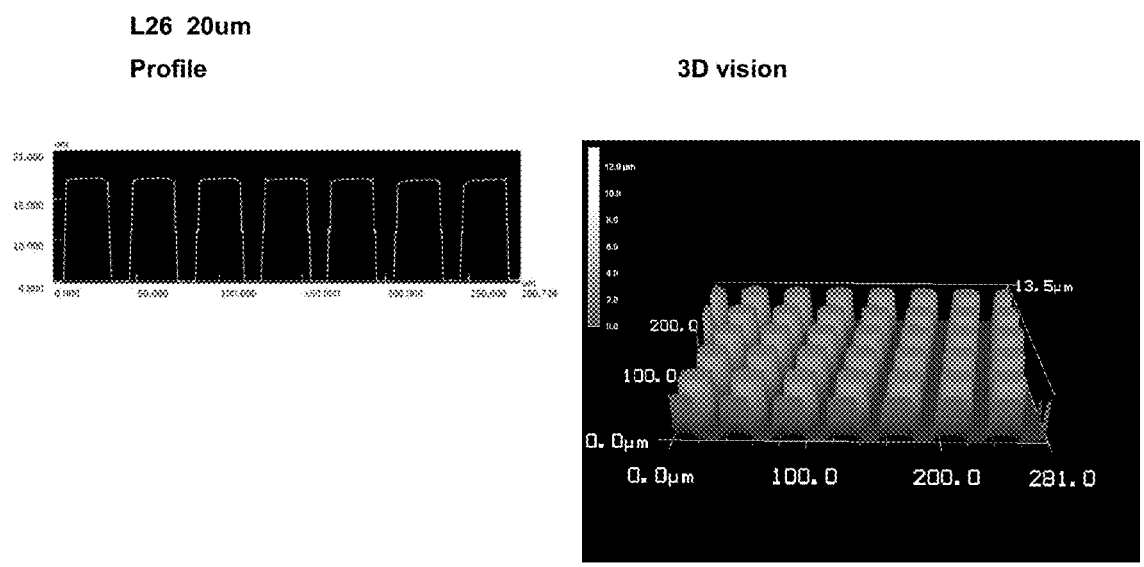
FIG. 20 is the 3D laser microscope imaging of a copper pillar with L26 as the leveler, pillar diameter=20 μm.
Figure 21:
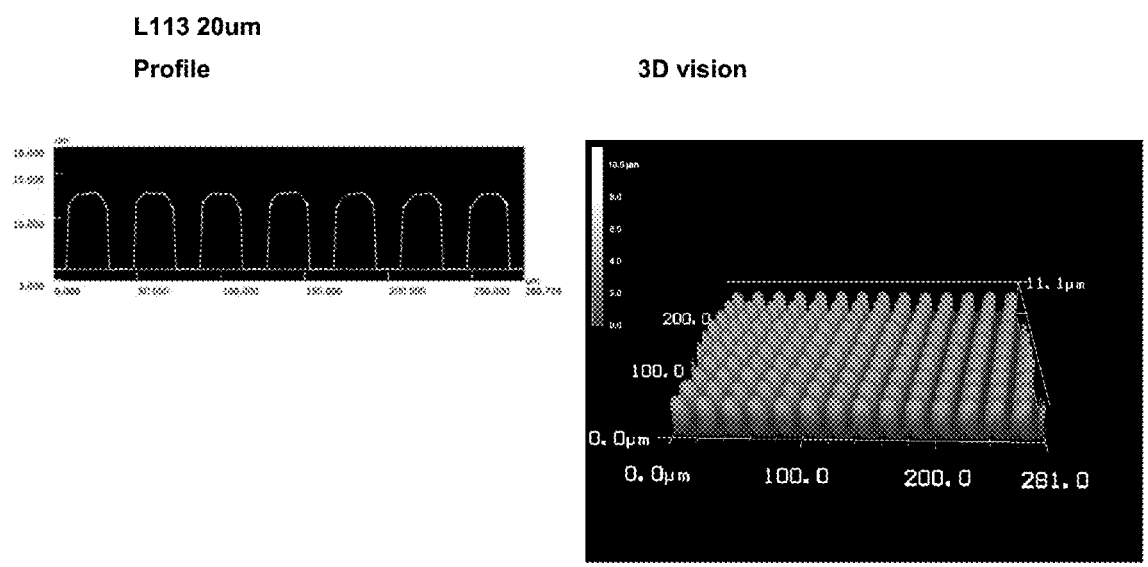
FIG. 21 is the 3D laser microscope imaging of a copper pillar with L113 as the leveler, pillar diameter=20 μm.
Figure 22:
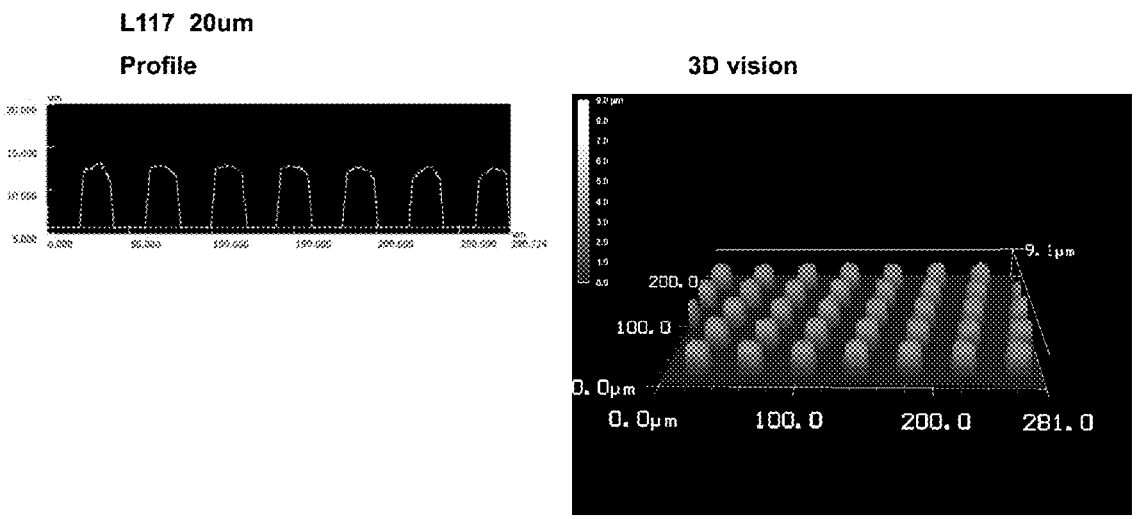
FIG. 22 is the 3D laser microscope imaging of a copper pillar with L117 as the leveler, pillar diameter=20 μm.

Example 4 (FIG. 7)

Comparative Electrolytic Copper Deposition Chemistry

An electrolytic copper plating composition of a conventional system was prepared having the following components and concentrations
   a. Copper ion from copper sulfate (50 g/L, $Cu^{2+}$)
   b. Sulfuric acid (100 g/L)
   c. Chloride ion (70 ppm)
   d. L26 (conventional leveler, 30 ppm)
   e. S24 (1000 ppm)
   f. A28 (10 ppm)

The electrolytic copper deposition chemistry was prepared according to the instructions of Table I. Plating conditions are summarized in Table II.

Example 5 (FIGS. 8, 11, 14, 17, 20, and 24)

Electrolytic Copper Deposition Chemistry of the Prior Art

An electrolytic copper plating composition of the invention was prepared having the following components and concentrations
   a. Copper ion from copper sulfate (50 g/L, $Cu^{2+}$)
   b. Sulfuric acid (100 g/L)
   c. Chloride ion (70 ppm)
   d. L26 (30 ppm)
   e. S24 (1000 ppm)
   f. A28 (10 ppm)

The electrolytic copper deposition chemistry was prepared according to the instructions of Table I. Plating conditions are summarized in Table III.

TABLE III

| | | Wafer Plating Conditions | | | |
|---|---|---|---|---|---|
| Plating area (cm2) | Target bump height (um) | Current density (ASD) | Current (mA) | Plating duration (min) | Agitation speed (rpm) |
| 0.21 | 50 | 10 | 21 | 22 | 110 |

Example 6 (FIGS. 9, 12, 15, 18, 21, and 25)

Electrolytic Copper Deposition Chemistry of the Invention

An electrolytic copper plating composition of the invention was prepared having the following components and concentrations
   a. Copper ion from copper sulfate (50 g/L, $Cu^{2+}$)
   b. Sulfuric acid (100 g/L)
   c. Chloride ion (70 ppm)
   d. L113 (30 ppm)
   e. S24 (1000 ppm)
   f. A28 (10 ppm)

The electrolytic copper deposition chemistry was prepared according to the instructions of Table I. Plating conditions are summarized in Table III.

Example 7 (FIGS. 10, 13, 16, 19, 22, and 26)

Electrolytic Copper Deposition Chemistry of the Invention (Preferred for Microbumps)

An electrolytic copper plating composition of the invention was prepared having the following components and concentrations
   a. Copper ion from copper sulfate (50 g/L, $Cu^{2+}$)
   b. Sulfuric acid (100 g/L)
   c. Chloride ion (70 ppm)
   d. L117 (30 ppm)
   e. S24 (1000 ppm)
   f. A28 (10 ppm)

Figure 23:
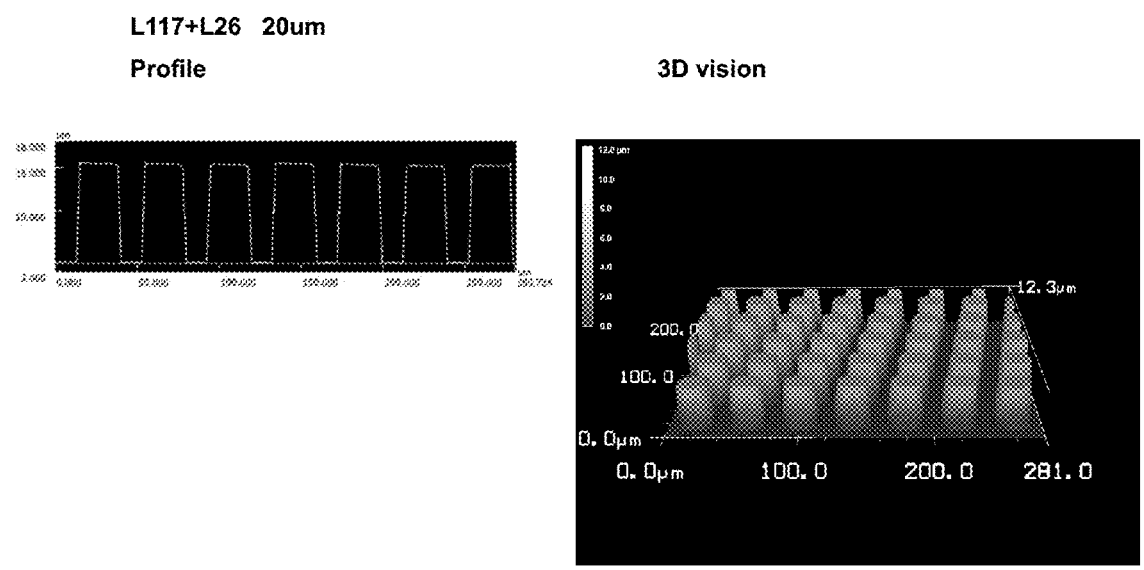
FIG. 23 is the 3D laser microscope imaging of a copper pillar with L117+L26 as the leveler, pillar diameter=20 μm.
Figure 24:
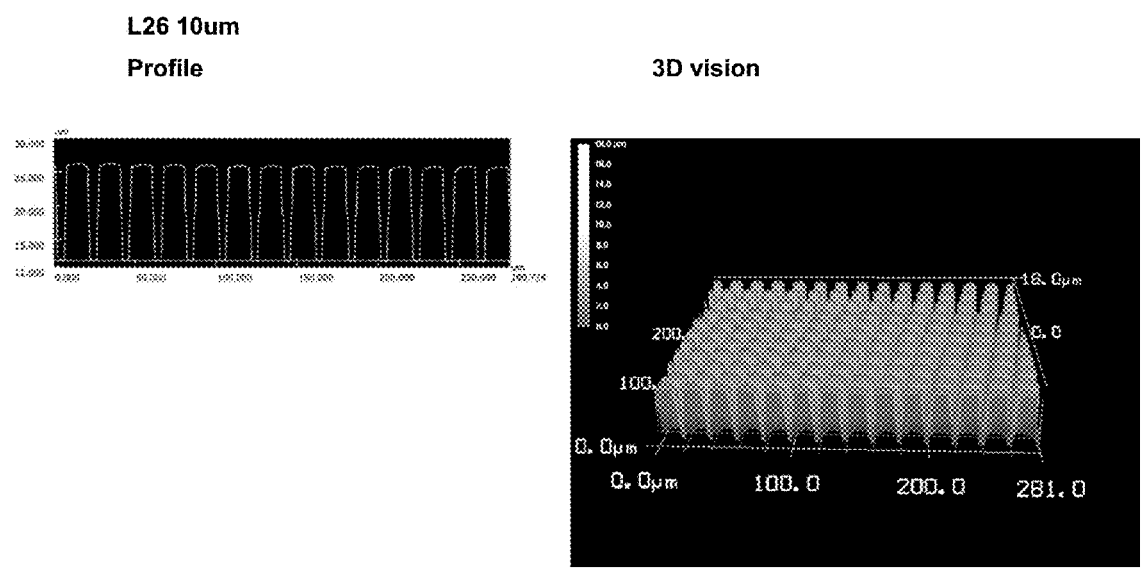
FIG. 24 is the 3D laser microscope imaging of a copper pillar with L26 as the leveler, pillar diameter=10 μm.
Figure 25:
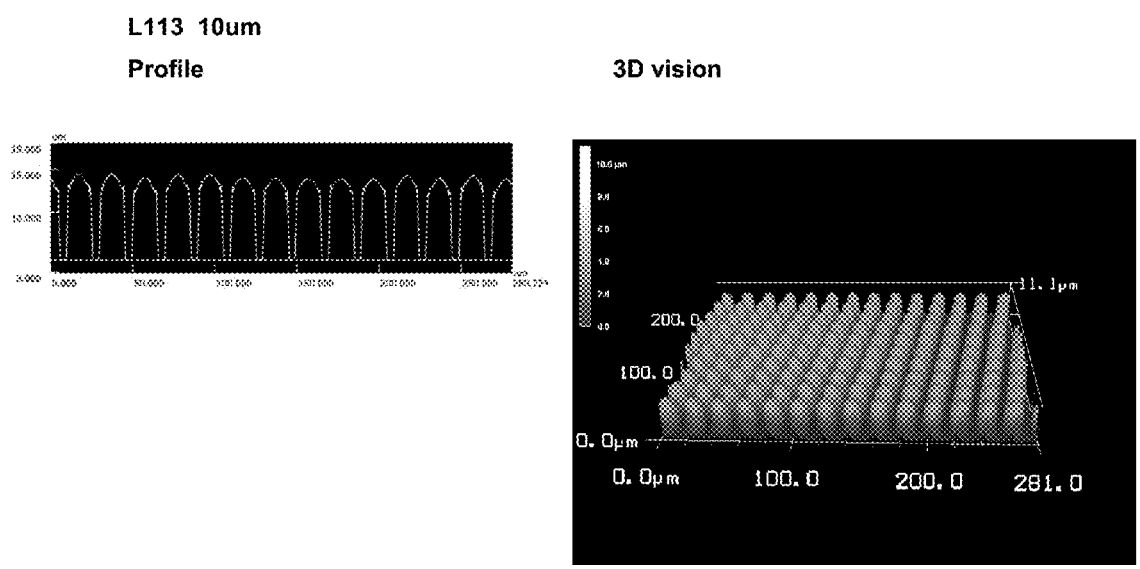
FIG. 25 is the 3D laser microscope imaging of a copper pillar with L113 as the leveler, pillar diameter=10 μm.
Figure 26:
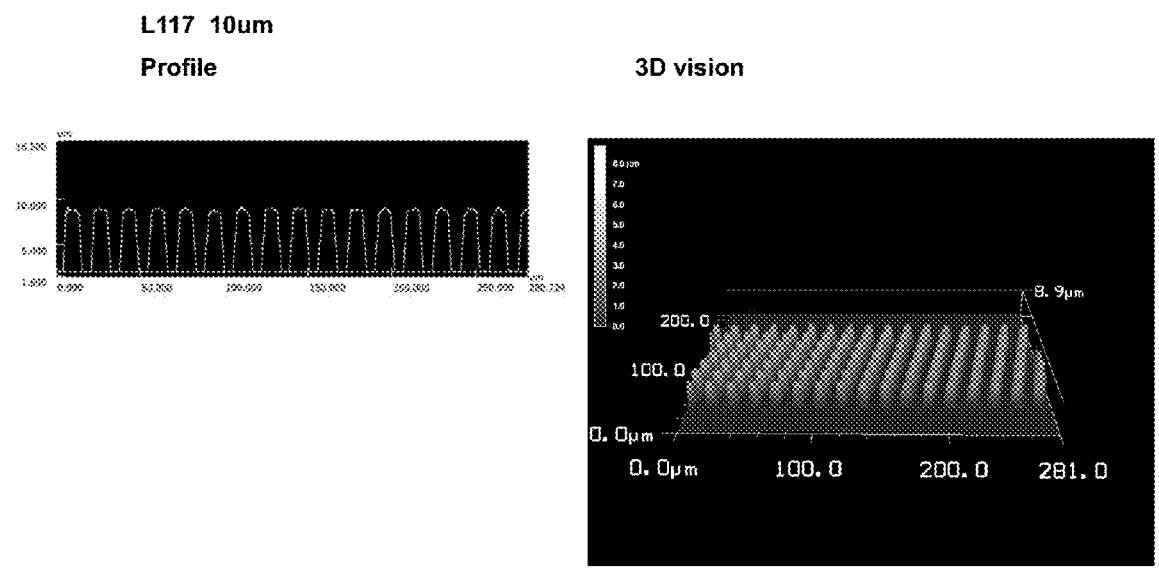
FIG. 26 is the 3D laser microscope imaging of a copper pillar with 117 as the leveler, pillar diameter=20 μm.
Figure 27:
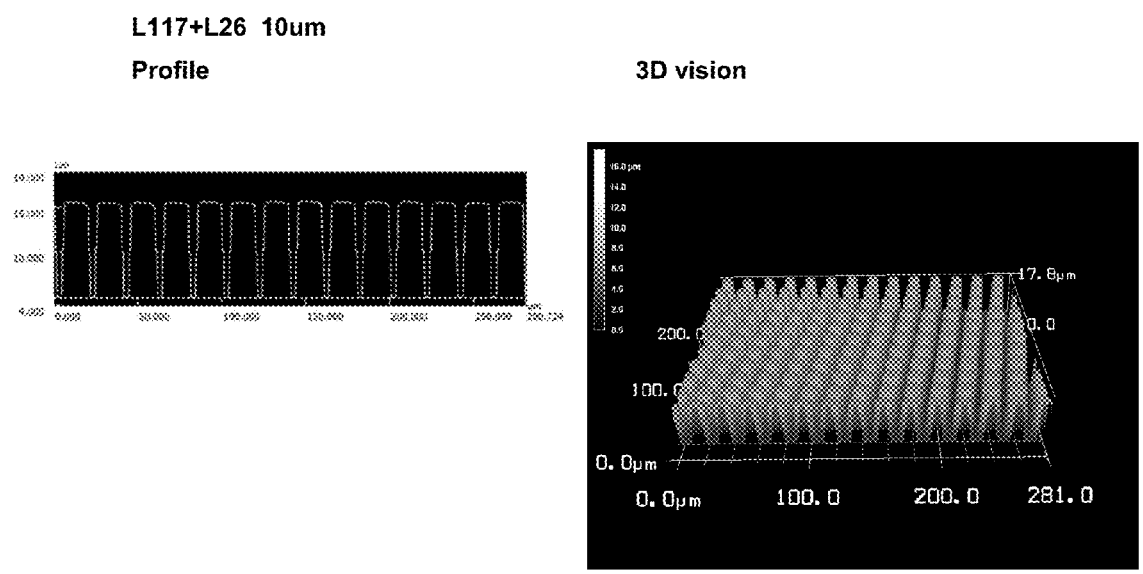
FIG. 27 is the 3D laser microscope imaging of a copper pillar with L117+L26 as the leveler, pillar diameter=10 μm.

The electrolytic copper deposition chemistry was prepared according to the instructions of Table I. Plating conditions are summarized in Table III Example 8 (FIGS. 23 and 27)

Electrolytic Copper Deposition Chemistry of the Invention (Preferred)

An electrolytic copper plating composition of the invention was prepared having the following components and concentrations
a. Copper ion from copper sulfate (50 g/L, $Cu^{2+}$)
b. Sulfuric acid (100 g/L)
c. Chloride ion (70 ppm)
d. L117 (9 ppm)+L26 (14 ppm)
e. S24 (1000 ppm)
f. A28 (10 ppm)

The electrolytic copper deposition chemistry was prepared according to the instructions of Table I. Plating conditions are summarized in Table III.

What is claimed is:

1. A method of electroplating comprising:
providing a substrate and an electrolytic plating composition;
contacting the substrate with the electrolytic plating composition; and
applying an electrical current to the electrolytic plating composition to deposit a metal layer onto the substrate;
wherein the metal layer has a predetermined topography, and
wherein the electrolytic plating composition includes a source of metal ions and a compound of formula (I):

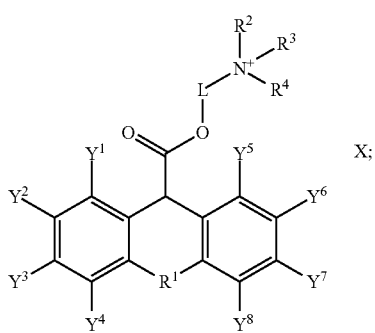

(I)

wherein X is $Cl^-$, or $Br^-$;
$R^1$ is O, S or N;
$R^2$, $R^3$ and $R^4$ are independently selected from the group consisting of hydrogen, unsubstituted or substituted alkyl, unsubstituted or substituted alkenyl, unsubstituted or substituted alkynyl, unsubstituted or substituted $C_{3-12}$cycloalkyl, unsubstituted or substituted $C_{6-12}$ aryl, unsubstituted or substituted 3-12 membered heterocyclic, and unsubstituted or substituted 5-12 membered heteroaryl; or $R^2$ and $R^3$ may combine with an atom or atoms to which they are attached to form unsubstituted or substituted $C_{3-12}$cycloalkyl, unsubstituted or substituted 3- to 12-membered heterocyclic, unsubstituted or substituted $C_{6-12}$ aryl, or unsubstituted or substituted 5- to 12-membered heteroaryl;
$Y^1$, $Y^2$, $Y^3$, $Y^4$, $Y^5$, $Y^6$, $Y^7$ and $Y^8$ are independently selected from the group consisting of hydrogen, halogen, unsubstituted or substituted alkyl, unsubstituted or substituted alkenyl, unsubstituted or substituted alkynyl, unsubstituted or substituted $C_{3-12}$cycloalkyl, unsubstituted or substituted $C_{6-12}$ aryl, unsubstituted or substituted 3-12 membered heterocyclic, and unsubstituted or substituted 5-12 membered heteroaryl; and
L is selected from the group consisting of unsubstituted or substituted alkyl, unsubstituted or substituted $C_{6-12}$ aryl, and unsubstituted or substituted 3- to 12-membered heterocyclyl.

2. The method of claim 1, wherein the metal layer has a flat topography, a convex topography, or a concave topography.

3. The method of claim 2, wherein the flat topography has a diameter ranging from about 5 microns to about 250 microns.

4. The method of claim 1, wherein the substrate has a diameter of 5 to 250 microns and an aspect ratio of 0.1 to 1.25, or a height of 5 to 300 microns.

5. The method of claim 4, wherein the substrate has a recess having a height of 5 to 30 microns.

6. The method of claim 1, wherein the substrate includes lines with a width of 10 nm to 20 microns, a length of 10 nm to 200 microns, and a thickness of 10 nm to 20 microns.

7. The method of claim 1, wherein the substrate is a semiconductor wafer or chip.

8. The method of claim 1, wherein $R^1$ in formula (I) is O.

9. The method of claim 1, wherein $Y^1$, $Y^2$, $Y^3$, $Y^4$, $Y^5$, $Y^6$, $Y^7$, and $Y^8$ in formula (I) are hydrogen.

10. The method of claim 1, wherein $R^2$, $R^3$ and $R^4$ in formula (I) are each independently $C_{1-6}$alkyl.

11. The method of claim 1, wherein $R^2$ in formula (I) is methyl, and $R^3$ and $R^4$ in formula (I) are isopropyl.

12. The method of claim 1, wherein in $R^2$ and $R^3$ in formula (I) are ethyl, and $R^4$ in formula (I) is benzyl.

13. The method of claim 1, wherein the electrolytic plating composition further includes an accelerator and a suppressor.

14. The method of claim 13, wherein the accelerator is of formula (IV):

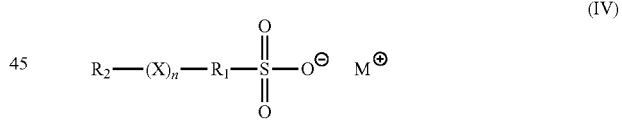

(IV)

wherein X is O or S;
n is 1 to 6;
M is hydrogen, alkali metal, or ammonium;
$R_1$ is an alkylene, cyclic alkylene group of 1 to 8 carbon atoms, or an aromatic hydrocarbon of 6 to 12 carbon atoms; and
$R_2$ is $MO_3SR_1$.

15. The method of claim 14, wherein X in formula (IV) is S.

16. The method of claim 13, wherein the suppressor is of formula (VIII):

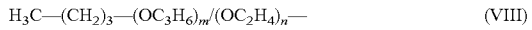

(VIII)

wherein n is between 1 and about 200 and m is between 1 and about 200.

* * * * *